US008209194B1

(12) United States Patent
Nidy et al.

(10) Patent No.: US 8,209,194 B1
(45) Date of Patent: Jun. 26, 2012

(54) METHOD AND SYSTEM FOR PROVIDING A HEALTHCARE EXPENSE DONATION NETWORK

(75) Inventors: Dawn M. Nidy, Belmont, CA (US);
Safia Ata Ali, San Francisco, CA (US);
Craig LaSalle, Los Altos, CA (US)

(73) Assignee: Intuit Inc., Mountain View, CA (US)

( * ) Notice: Subject to any disclaimer, the term of this patent is extended or adjusted under 35 U.S.C. 154(b) by 173 days.

(21) Appl. No.: 12/845,309

(22) Filed: Jul. 28, 2010

(51) Int. Cl.
*G06Q 40/00* (2006.01)
*G06Q 50/00* (2006.01)

(52) U.S. Cl. ......... 705/2; 705/3; 705/4; 705/35; 705/37; 705/40

(58) Field of Classification Search .................. 705/2–4, 705/35, 37, 40
See application file for complete search history.

(56) References Cited

U.S. PATENT DOCUMENTS

| 7,765,146 | B2 * | 7/2010 | Sakaue et al. ............... 705/37 |
| 2002/0038225 | A1 * | 3/2002 | Klasky et al. ................. 705/1 |
| 2006/0253365 | A1 * | 11/2006 | Langshur et al. ............. 705/37 |
| 2006/0259424 | A1 * | 11/2006 | Turcotte et al. .............. 705/40 |

* cited by examiner

*Primary Examiner* — Gerald J. O'Connor
*Assistant Examiner* — Mark Holcomb
(74) *Attorney, Agent, or Firm* — McKay and Hodgson, LLP; Philip McKay; Sean P. Lewis

(57) ABSTRACT

A method and system for providing a healthcare expense donation network whereby a third party provided healthcare management system, such as a computing system or on-line implemented healthcare expense tacking and/or payment system provides a service through which a healthcare consumer can create a verified patient need profile indicating a need for help in paying their healthcare expenses and requesting donations to this end. At least part of the healthcare consumer's patient need profile data is verified, as well as any other financial and/or personal data associated with the submitted patient need profile that a potential donor, the patient, and/or the provider of the process for providing a healthcare expense donation network desires to be verified. Once the healthcare patient need profile data is verified, the verified patient need profile is made available to potential donors and the potential donors are provided the ability to securely make donations to the patient's healthcare expenses directly.

36 Claims, 2 Drawing Sheets

METHOD AND SYSTEM FOR PROVIDING A HEALTHCARE EXPENSE DONATION NETWORK

BACKGROUND

Most healthcare consumers are keenly aware that healthcare costs have risen dramatically over the past decade. For many people, this increase in healthcare costs means that any prolonged, chronic, or serious illness/injury can easily result in healthcare expenses that are simply beyond their capability to pay. Indeed, it is currently estimated that healthcare related expenses contribute, if not cause, 62% of the personal bankruptcies filed in the United States each year.

Not only is the situation described above problematic for the healthcare consumers who cannot pay their healthcare expenses, it is also a significant problem for healthcare service provides who currently end up writing off up to 50% of the patient portion of funds owed to them after patient healthcare insurance plans have paid their share. This situation for the healthcare service providers is further aggravated by the fact that the healthcare services industry has some of the highest invoice processing costs of any industry, often on the order of 15% of the invoiced amount.

Given the nature of healthcare expenses, and the gravity of the situation described above, particularly for the patients/healthcare consumers, there are many individuals and/or organizations that would be willing to help patients/healthcare consumers with their healthcare expenses if: the potential donors were made aware of specific situations and/or patients in need; the potential donors could verify the patients' bills and verify that their donations were being made for legitimate causes; and the potential donors had a relatively easy way to facilitate providing funds and ensuring the funds were used to help pay the patients' healthcare expenses.

While the contributions from these potential donors are sorely needed and would unquestionable help many patients, there is currently no effective or efficient system for helping these potential donors become aware of specific and verified patients in need, or for providing the donors an efficient method for making donations to the healthcare service providers to whom the patient owes the funds. Consequently, many patients are currently forced into financial dire straits by healthcare expenses while, at the same time, many potentially willing donors are unaware of the patients' situations and/or feel they have no easy way of verifying a patient's need or of easily making payment to the healthcare providers on behalf of a patient. Clearly this is a less than ideal situation for all parties involved.

SUMMARY

In accordance with one embodiment, a method and system for providing a healthcare expense donation network includes a process for providing a healthcare expense donation network whereby, in one embodiment, a third party provided healthcare management system, such as a computing system or on-line implemented healthcare expense tacking and/or payment system, provides a service through which a healthcare consumer can create a patient need profile indicating a need for help in paying their healthcare expenses and requesting donations to this end. In one embodiment, the healthcare consumer's healthcare expenses are verified, as well as any other financial and/or personal data associated with the submitted patient need profile that potential donors, the patients, and/or the provider of the process for providing a healthcare expense donation network desires to be verified. In one embodiment, once the healthcare consumer's healthcare expenses, and/or other patient need profile data, are verified, the patient need profile is made available to potential donors including, but not limited to: the healthcare service provider to whom the funds are owed; potential donors designated by the healthcare consumer, such as family and friends; pre-registered potential donors that have indicated a desire to help specific verified types of patients and/or healthcare consumers with verified healthcare expense needs; pre-registered potential donors who have indicated a desire to help any verified patients and/or healthcare consumers with any verified healthcare expense needs; and/or various other potential donor parties and/or organizations associated with specific types of patients/healthcare needs or general patient/healthcare assistance. In one embodiment, the potential donors are provided the ability to securely make donations to the patient's healthcare expenses directly, in one embodiment, through the notification of need and attached patient need profile. In one embodiment, any funds so contributed by a donor are forwarded directly to the healthcare provider to whom the money is owed and the patient is informed of the deposited funds and any remaining balance. In one embodiment, an updated balance of funds owed is included in the patient need profile. In one embodiment, any donors making a donation are provided documentation data indicating the donation, the remaining balance, and any data required for tax purposes.

Using the method and system for providing a healthcare expense donation network, as discussed herein, potential donors are made aware of specific patients in need, whose situations and healthcare expenses are verified through a third party, and the donors are provided an efficient and user friendly way to facilitate providing funds to help the patients with their healthcare expenses and ensuring that the funds are actually used to help pay the patients healthcare expenses by transferring the funds directly to the healthcare service providers to whom the funds are owed. Consequently, using the method and system for providing a healthcare expense donation network, as discussed herein, potential donors are more likely to become actual donors and more needy patients will be provided the funds they need to avoid financial ruin.

As discussed in more detail below, using the below embodiments, with little or no modification and/or user input, there is considerable flexibility, adaptability, and opportunity for customization to meet the specific needs of various users under numerous circumstances.

Figure 1:
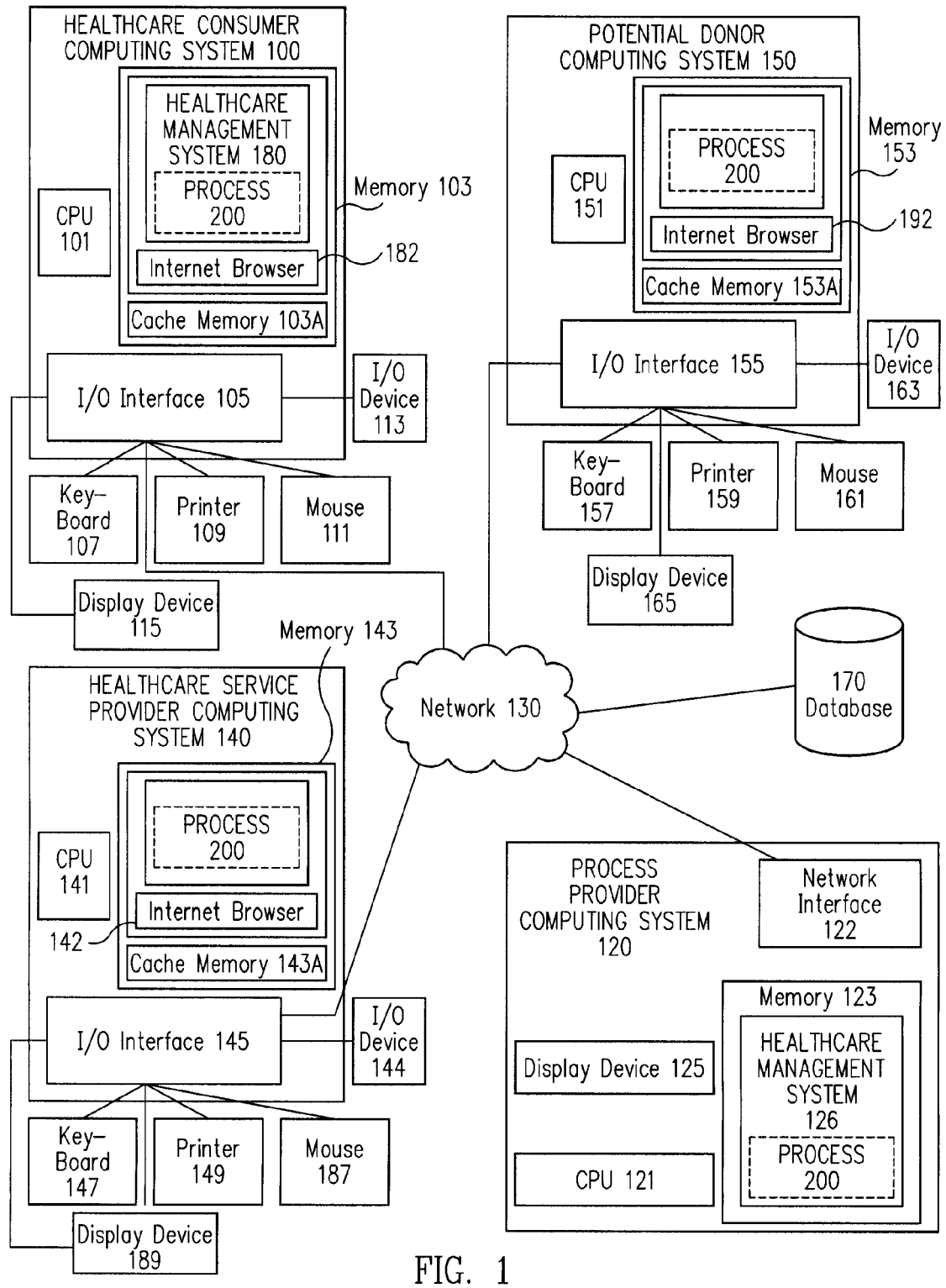
FIG. 1 is a block diagram of an exemplary hardware architecture for implementing one embodiment.

Common reference numerals are used throughout the FIG.s and the detailed description to indicate like elements. One skilled in the art will readily recognize that the above FIG.s are examples and that other architectures, modes of operation, orders of operation and elements/functions can be provided and implemented without departing from the characteristics and features of the invention, as set forth in the claims.

DETAILED DESCRIPTION

Embodiments will now be discussed with reference to the accompanying FIG.s, which depict one or more exemplary embodiments. Embodiments may be embodied in many different forms and should not be construed as limited to the embodiments set forth herein, shown in the FIG.s, and/or described below. Rather, these exemplary embodiments are provided to allow a complete disclosure that conveys the principles of the invention, as set forth in the claims, to those of skill in the art.

Some embodiments are implemented in a computing system including a conventional computing system running a conventional operating system such as those distributed by Microsoft Corporation of Redmond Wash.; Apple Computer Inc. of Cupertino Calif.; any Unix operating system; any Linux operating system; the Palm OS series of operating systems; or any other operating system designed to generally manage operations on a computing system, whether known at the time of filing or as developed later. Some embodiments are implemented in a mobile computing system running mobile operating systems such as Symbian® OS, Windows® Mobile, Android™ or any other operating system designed to generally manage operations on a mobile computing system, whether known at the time of filing or as developed later. As described more fully below, embodiments can be implemented on computing systems other than a conventional computing system such as, for example, a personal digital assistant, a cell phone, a smart phone, or other computing system capable of processing computer readable data, whether known at the time of filing or as developed later. Computing systems also include those in which one or more computing resources (hardware or software) are located remotely and accessed via a cloud computing environment and/or network, such as a Local Area Network (LAN), Wide Area Network (WAN), a public network, such as the Internet, a private network, a combination of network types, a computing system bus, or other electronic medium in which data may be exchanged between one computing system and one or more other computing system(s), whether known at the time of filing or as developed later. Embodiments may be included as add-on software for existing software programs, packages or applications, and embodiments may be a feature of an application that is bundled with a computing system or sold separately. Some embodiments may also be implemented as functionality embedded in hardware devices and systems.

Output generated by one or more embodiments can be displayed on a display screen, delivered from a website and/or web-based function, transmitted to a remote device, stored on any database, computer server or other storage mechanism, printed, or used in any other way. In addition, in some embodiments, processes and/or systems described herein may make use of input provided to the computer device implementing a process and/or application, discussed herein, via user interface devices such as a keyboard, mouse, touchpad, or any other device capable of providing user input to a computing system or for translating user actions into computing system operations, whether known at the time of filing or as developed later.

In accordance with one embodiment, a method and system for providing a healthcare expense donation network includes a process for providing a healthcare expense donation network whereby, in one embodiment, a third party provided healthcare management system, such as a computing system or on-line implemented healthcare expense tacking and/or payment system, provides a service through which a healthcare consumer can create a patient need profile indicating a need for help in paying their healthcare expenses and requesting donations to this end. In one embodiment, the healthcare consumer's healthcare expenses are verified, as well as any other financial and/or personal data associated with the submitted patient need profile that potential donors, the patients, and/or the provider of the process for providing a healthcare expense donation network desires to be verified. In one embodiment, once the healthcare consumer's healthcare expenses, and/or other patient need profile data, are verified, the patient need profile is made available to potential donors including, but not limited to: the healthcare service provider to whom the funds are owed; potential donors designated by the healthcare consumer, such as family and friends; pre-registered potential donors that have indicated a desire to help specific verified types of patients and/or healthcare consumers with verified healthcare expense needs; pre-registered potential donors who have indicated a desire to help any verified patients and/or healthcare consumers with any verified healthcare expense needs; and/or various other potential donor parties and/or organizations associated with specific types of patients/healthcare needs or general patient/healthcare assistance. In one embodiment, the potential donors are provided the ability to securely make donations to the patient's healthcare expenses directly, in one embodiment, through the notification of need and attached patient need profile. In one embodiment, any funds so contributed by a donor are forwarded directly to the healthcare provider to whom the money is owed and the patient is informed of the deposited funds and any remaining balance. In one embodiment, an updated balance of funds owed is included in the patient need profile. In one embodiment, any donors making a donation are provided documentation data indicating the donation, the remaining balance, and any data required for tax purposes.

In one embodiment a healthcare management system is provided by a healthcare management system provider such as any computing system and/or on-line healthcare management system, as defined herein, known in the art at the time of filing, and/or as developed thereafter.

The term healthcare management system, as used herein, includes, but is not limited to a computing system and/or on-line implemented system that helps a user healthcare consumer track their healthcare expenses by gathering healthcare expense data from one or more sources, such as invoices, EOBs, and financial transaction records, and then organizing, categorizing, and/or displaying the data in one or more summary displays and/or reports. Specific examples of currently available healthcare management systems include, but are not limited to: Quicken Health Expense Tracker™, available from Intuit Inc. of Mountain View, Calif.; Intuit Health Bill Pay™ available from Intuit Inc. of Mountain View, Calif.; and/or any other computing system implemented and/or on-line healthcare management applications, programs, or systems, as discussed herein, and or as known in the art at the time of filing, and/or as developed after the time of filing.

In one embodiment, the healthcare management system is provided by a healthcare management system provider who is a third party, i.e., is neither the healthcare consumer nor the healthcare service provider. In one embodiment the healthcare management system is provided by a healthcare management system provider who is also the provider of at least part of the process for providing a healthcare expense donation network discussed herein.

In one embodiment, a healthcare consumer is provided access to the healthcare management system via a healthcare consumer computing system and the healthcare consumer is provided data indicating current or estimated healthcare services fees owed/to be owed for healthcare services provided to a patient associated with the healthcare consumer.

In one embodiment, the healthcare consumer views data indicating current or estimated healthcare services fees owed/ to be owed for healthcare services provided to a patient associated with the healthcare consumer obtained from invoices, EOB data, healthcare benefit plan providers, or any other source of actual and/or estimated healthcare service fees owed/to be owed by the healthcare service consumer after any healthcare benefit plans have paid their share, i.e. the healthcare consumer's "out-of-pocket" costs.

In one embodiment, after viewing the data indicating current or estimated healthcare services fees owed/to be owed for healthcare services provided to a patient associated with the healthcare consumer through the healthcare management system, the healthcare services consumer determines that they cannot afford to pay all, or part of, the healthcare services fees owed/to be owed.

In one embodiment, the healthcare consumer is provided a link through the healthcare management system to a patient need profile data entry screen. In one embodiment, the patient need profile data entry screen requests various patient need profile data from the healthcare consumer such as, but not limited to, any one or more of: the patient's name, age, DOB, demographic data, etc.; the patient's illness/injury associated with the healthcare service expenses owed; the providers of the healthcare services for which funds are owed; images of the patient, the patient's family and/or the healthcare consumer; how much the healthcare consumer has already paid; how much is owed; any healthcare benefit plans associated with the patient/healthcare consumer; biographical and/or historical information associated with the healthcare consumer, the patient, the family, etc.; financial data associated with the healthcare consumer, such as income, savings, assets etc.; contact data, e-mail, phone, address, etc., associated with any potential donors known by the healthcare consumer, such as family and friends; data granting the process for providing a healthcare expense donation network, a provider of the process for providing a healthcare expense donation network, or any other party associated with the process for providing a healthcare expense donation network, permission to obtain and/or verify any of the patient need profile data provided by the healthcare consumer from any party or source; and/or any other data desired by the patient, the healthcare consumer, potential donors, and/or the healthcare management system provider.

In one embodiment, the healthcare consumer submits the patient need profile data to the healthcare management system provider through the patient need profile data entry screen and/or the healthcare management system.

In one embodiment, at least part of the patient need profile data is verified by the healthcare management system and/or healthcare management system provider. In one embodiment, at least part of the patient need profile data is verified by the healthcare management system and/or healthcare management system provider by contacting the healthcare service provider owed the funds and/or any healthcare benefit plan providers involved.

As noted above, in some embodiments, the healthcare management system, helps a user healthcare consumer track their healthcare expenses by gathering healthcare expense data from one or more sources, such as invoices, EOBs, and financial transaction records, and then organizing, categorizing, and/or displaying the data in one or more summary displays and/or reports. Consequently, in some embodiments, the healthcare management system and/or healthcare management system provider already have access to at least part of the healthcare consumer's data.

In addition, in some instances, the healthcare management system and/or the process for providing a healthcare expense donation network is associated with one or more other data management systems, such as, but not limited to: computing system implemented accounting and/or invoicing systems, packages, programs, modules, or applications; personal financial management systems, packages, programs, modules, or applications; financial management systems, packages, programs, modules, or applications; computing system implemented banking systems, packages, programs, modules, or applications; computing system implemented personal and small business financial management systems, packages, programs, modules, or applications; computing system implemented business systems, packages, programs, modules, or applications; computing system implemented marketing device distribution systems, packages, programs, modules, or applications; computing system implemented financial institution financial management systems, packages, programs, modules, or applications; computing system implemented tax preparation systems, packages, programs, modules, or applications; computing system implemented business and/or point of sale systems, packages, programs, modules, or applications; computing system implemented healthcare management systems, packages, programs, modules, or applications and various other electronic data driven data management systems, packages, programs, modules, or applications, whether known at the time of filing or as developed later. Consequently, in some embodiments, the healthcare management system and/or healthcare management system provider can readily obtain access to at least part of the healthcare consumer's data, including the general financial data associated with the healthcare consumer, to verify that the healthcare consumer not only has genuine and verified healthcare expenses, but also has a genuine and verified financial need.

In one embodiment, at least part of the patient need profile data is verified by the healthcare management system and/or healthcare management system provider using any data verification means, procedure, process, and/or source, as discussed herein, and/or as known in the art at the time of filing, and/or as developed after the time of filing.

In one embodiment, at least part of the patient need profile data, and the verified patient need profile data, is processed by one or more processors associated with one or more computing systems and transformed into a verified patient need profile.

In various embodiments, the verified patient need profile includes, but is not limited to, any one or more of: data indicating the patient's name, age, DOB, demographic data etc.; data indicating the patient's illness/injury associated with the healthcare service expenses owed; data indicating the providers of the healthcare services for which funds are owed; data indicating biographical and/or historical information associated with the healthcare consumer, the patient, the family, etc.; data indicating the financial need associated with the healthcare consumer, such as income, savings, assets etc. contact data; data indicating which portion of the verified patient need profile data has been verified; data indicating an updated balance of amounts owed; data indicating how much the healthcare consumer has already paid themselves; any images submitted by the healthcare consumer of the patient, patient's family and/or the healthcare consumer; and/or any other data desired by the patient, the healthcare consumer, potential donors, and/or the healthcare management system provider.

In one embodiment data representing the verified patient need profile is stored by any one of various data storage means and using any data storage mechanism as discussed herein, and/or as known in the art at the time of filing, and/or as developed after the time of filing.

In one embodiment, one or more payment mechanisms are established by, and/or through, the healthcare management system and/or healthcare management system provider. In one embodiment, the one or more payment mechanisms are established to provide a potential donor a means for making a payment to a healthcare service provider to whom the healthcare consumer owes the funds on behalf of the healthcare consumer, and through the healthcare management system and/or a provided verified patient need profile, without having to access any other site or contact any other third party, i.e., through a single action through a single, and in one embodiment, secure, interface.

In one embodiment, the one or more payment mechanisms established by, and/or through, the healthcare management system and/or healthcare management system provider include, but are not limited to, setting up a merchant account for the healthcare service provider, in one embodiment through the healthcare management system.

In one embodiment, the one or more payment mechanisms established by, and/or through, the healthcare management system and/or healthcare management system provider include, but are not limited to, setting up a patient/healthcare consumer account for the healthcare service provider, in one embodiment through the healthcare management system, and then transferring the funds to the healthcare service provider, in one embodiment through the healthcare management system.

In one embodiment, the one or more payment mechanisms established by, and/or through, the healthcare management system and/or healthcare management system provider include, but are not limited to, the healthcare management system and/or healthcare management system provider acting in the role of clearing house to ensure that various donations by various donors made on behalf of various healthcare consumers are transferred to the respective healthcare service providers.

In one embodiment, the verified patient need profile is provided to one or more potential donors. In one embodiment, the verified patient need profile is provided to one or more potential donors through the healthcare management system and/or healthcare management system provider.

In one embodiment, the verified patient need profile is first provided to the healthcare service provider to whom the healthcare consumer owes the funds to provide the healthcare service provider the opportunity to publicly, or privately, discount the amount owed; thereby acting in the role of a first potential donor. In one embodiment, any discount afforded the healthcare consumer by the healthcare service provider is shown in the verified patient need profile.

In one embodiment, the verified patient need profile is provided to any potential donors identified by the healthcare consumer, such as family and friends, in the patient need profile data input screen.

In one embodiment, the verified patient need profile is provided to pre-registered potential donors that have indicated a desire to help specific verified types of patients and/or healthcare consumers with verified healthcare expense needs.

In one embodiment, the verified patient need profile is provided to pre-registered potential donors who have indicated a desire to help any verified patients and/or healthcare consumers with any verified healthcare expense needs.

In one embodiment, the verified patient need profile is provided to various other potential donor parties and/or organizations associated with specific types of patients/healthcare needs or general patient/healthcare assistance.

In one embodiment, the verified patient need profile is provided via a network and/or one or more computing systems as discussed herein, and/or as known in the art at the time of filing, and/or as developed after the time of filing.

In one embodiment, the verified patient need profile includes a link and/or donation entry screen/field, through which a donor can donate funds, or indicate a desire to donate funds, to the healthcare service provider to whom the healthcare consumer owes funds on behalf of the healthcare consumer.

In one embodiment, at least one donor indicates a desire to donate funds to the healthcare service provider to whom the healthcare consumer owes funds on behalf of the healthcare consumer and indicates the amount to be donated.

In one embodiment, the funds are collected via credit card, wire transfer, bank transfer, bill pay, check, PayPal™, or any other method, means, and or mechanism for transferring funds as discussed herein, and/or as known in the art at the time of filing, and/or as developed after the time of filing.

In one embodiment the donated funds are then transferred to the healthcare services provider by any of the one or more payment mechanisms established by, and/or through, the healthcare management system and/or healthcare management system provider discussed above.

In one embodiment, any funds so contributed by a donor are forwarded directly to the healthcare provider to whom the money is owed and the patient is informed of the deposited funds and any remaining balance.

In one embodiment, an updated balance of funds owed is included in the patient need profile.

In one embodiment, any donors making a donation are provided documentation data indicating the donation, the remaining balance, and any data required for tax purposes.

Hardware System Architecture

FIG. 1 is a block diagram of an exemplary hardware architecture for implementing one embodiment of a process for providing a healthcare expense donation network, such as exemplary process 200 (FIG. 2) discussed herein, that, returning to FIG. 1, includes: a healthcare consumer computing system 100, e.g., a first computing system; a donor computing system 150, e.g., a second computing system; a healthcare service provider computing system 140, e.g., a third computing system; a process provider computing system 120, e.g., a fourth computing system; and a database 170, all operatively coupled by a network 130.

As seen in FIG. 1, healthcare consumer computing system 100 typically includes a central processing unit (CPU) 101, an input/output (I/O) interface 105, and a memory system 103, including cache memory 103A. In one embodiment, memory system 103 includes all, or part, of a healthcare management system 180, such as any computing system and/or on-line healthcare management system, as defined herein, known in the art at the time of filing, and/or as developed thereafter.

The term healthcare management system, as used herein, includes, but is not limited to a computing system and/or on-line implemented system that helps a user healthcare consumer track their healthcare expenses by gathering healthcare expense data from one or more sources, such as invoices, EOBs, and financial transaction records, and then organizing, categorizing, and/or displaying the data in one or more summary displays and/or reports. Specific examples of currently available healthcare management systems include, but are not limited to: Quicken Health Expense Tracker™, available from Intuit Inc. of Mountain View, Calif.; Intuit Health Bill Pay™ available from Intuit Inc. of Mountain View, Calif.; and/or any other computing system implemented and/or on-line healthcare management applications, programs, or systems, as discussed herein, and or as known in the art at the time of filing, and/or as developed after the time of filing.

In one embodiment, healthcare management system 180 is stored, in whole, or in part, in memory system 103, and is used by, or includes, or is accessed by, process for providing a healthcare expense donation network 200 and/or a given individual.

Returning to FIG. 1, healthcare consumer computing system 100 may further include standard user interface devices such as a keyboard 107, a mouse 111, a printer 109, and a display device 115, as well as, one or more standard input/output (I/O) devices 113, such as a compact disk (CD) or Digital Video Disc (DVD) drive, floppy disk drive, or other digital or waveform port, or other device capable of inputting data to, and outputting data from, healthcare consumer computing system 100, whether available or known at the time of filing or as later developed. As discussed in more detail below, in one embodiment, process for providing a healthcare expense donation network 200, and/or healthcare management system 180, are entered, in whole, or in part, into healthcare consumer computing system 100 via I/O device 113, such as from a CD, DVD, floppy disk, portable hard drive, memory stick, download site, or other medium and/or computer program product as discussed herein.

In one embodiment, healthcare consumer computing system 100 also includes an Internet browser capability 182 that, in one embodiment, includes a search engine (not shown) and is stored, in whole, or in part in memory 103.

In one embodiment, patient need profile data associated with a given healthcare consumer is created through process for providing a healthcare expense donation network 200 and/or stored, in whole, or in part, in memory system 103, and is used by, or is accessed by process for providing a healthcare expense donation network 200 and/or one or more users. In one embodiment, healthcare consumer computing system 100 is a computing system accessible by one or more users. In one embodiment, healthcare consumer computing system 100 is used, and/or accessible, by another computing system, such as computing systems 120, 150 and/or 140 (discussed below).

In one embodiment, healthcare consumer computing system 100 is used, controlled, provided, and/or otherwise associated with a given healthcare consumer and/or a patient and/or an authorized user that is a representative of the given healthcare consumer or patient, and data representing all, or part, of healthcare expense and profile data associated with the given healthcare consumer or patient, is stored in healthcare consumer computing system 100.

Healthcare consumer computing system 100 can be any computing system as discussed herein and/or as known in the art at the time of filing and/or as developed thereafter, that includes components that can execute all, or part, of a process for providing a healthcare expense donation network, and/or a healthcare management system, in accordance with at least one of the embodiments as described herein.

As also seen in FIG. 1, donor computing system 150 typically includes a central processing unit (CPU) 151, an input/output (I/O) interface 155, and a memory system 153, including cache memory 153A. In one embodiment, memory system 153 includes all, or part, of process for providing a healthcare expense donation network 200.

Returning to FIG. 1, donor computing system 150 may further include standard user interface devices such as a keyboard 157, a mouse 161, a printer 159, and a display device 165, as well as, one or more standard input/output (I/O) devices 163, such as a compact disk (CD) or Digital Video Disc (DVD) drive, floppy disk drive, or other digital or waveform port, or other device capable of inputting data to, and outputting data from, donor computing system 150, whether available or known at the time of filing or as later developed. As discussed in more detail below, in one embodiment, process for providing a healthcare expense donation network 200 is entered, in whole, or in part, into donor computing system 150 via I/O device 163, such as from a CD, DVD, floppy disk, portable hard drive, memory stick, download site, or other medium and/or computer program product as discussed herein.

In one embodiment, donor computing system 150 also includes an Internet browser capability 192 that, in one embodiment, includes a search engine (not shown) and is stored, in whole, or in part in memory 153.

In one embodiment, patient need profile data associated with a given healthcare consumer is provided to donor computing system 150 through process for providing a healthcare expense donation network 200 and/or stored, in whole, or in part, in memory system 153, and is used by, or is accessed by, one or more donors. In one embodiment, donor computing system 150 is a computing system accessible by one or more users. In one embodiment, donor computing system 150 is used, and/or accessible, by another computing system, such as computing systems 120, 100, and/or 140 (discussed below).

In one embodiment, donor computing system 150 is used, controlled, provided, and/or otherwise associated with a given donor and/or an authorized user that is a representative of the given donor, and data representing all, or part, of healthcare expense and profile data associated with a given healthcare consumer or patient, is stored in donor computing system 150.

Donor computing system 150 can be any computing system as discussed herein and/or as known in the art at the time of filing and/or as developed thereafter, that includes components that can execute all, or part, of a process for providing a healthcare expense donation network, and/or a healthcare management system, in accordance with at least one of the embodiments as described herein.

As also seen in FIG. 1, healthcare service provider computing system 140 typically includes a central processing unit (CPU) 141, an input/output (I/O) interface 145, and a memory system 143, including cache memory 143A. In one embodiment, memory system 143 includes all, or part, of process for providing a healthcare expense donation network 200.

Returning to FIG. 1, healthcare service provider computing system 140 may further include standard user interface devices such as a keyboard 147, a mouse 187, a printer 149, and a display device 189, as well as, one or more standard input/output (I/O) devices 144, such as a compact disk (CD) or Digital Video Disc (DVD) drive, floppy disk drive, or other digital or waveform port, or other device capable of inputting data to, and outputting data from, healthcare service provider computing system 140, whether available or known at the time of filing or as later developed. As discussed in more detail below, in one embodiment, process for providing a healthcare expense donation network 200 is entered, in whole, or in part, into healthcare service provider computing system 140 via I/O device 144, such as from a CD, DVD, floppy disk, portable hard drive, memory stick, download site, or other medium and/or computer program product as discussed herein.

In one embodiment, healthcare service provider computing system 140 also includes an Internet browser capability 142 that, in one embodiment, includes a search engine (not shown) and is stored, in whole, or in part in memory 143.

In one embodiment, patient need profile data associated with a given healthcare consumer is provided to healthcare service provider computing system 140 through process for providing a healthcare expense donation network 200 and/or stored, in whole, or in part, in memory system 143, and is used by, or is accessed by, one or more agents for the healthcare service provider. In one embodiment, healthcare service provider computing system 140 is a computing system accessible by one or more users. In one embodiment, healthcare service provider computing system 140 is used, and/or accessible, by another computing system, such as computing systems 120, 100, and/or 150 (discussed below).

In one embodiment, healthcare service provider computing system 140 is used, controlled, provided, and/or otherwise associated with a given healthcare service provider to with whom the healthcare consumer has an account and/or to whom the healthcare consumer owes funds, and data representing all, or part, of the funds owed to the healthcare service provider by the healthcare consumer is stored in healthcare service provider computing system 140.

Healthcare service provider computing system 140 can be any computing system as discussed herein and/or as known in the art at the time of filing and/or as developed thereafter, that includes components that can execute all, or part, of a process for providing a healthcare expense donation network, and/or a healthcare management system, in accordance with at least one of the embodiments as described herein.

Also shown in FIG. 1 is database 170. In one embodiment, database 170 is a data storage device, a designated server system or computing system, or a designated portion of one or more server systems or computing systems, such as computing systems 100, 120, 140, 150, or a distributed database, or an external and/or portable hard drive. In one embodiment, database 170 is a dedicated mass storage device implemented in software, hardware, or a combination of hardware and software. In one embodiment, database 170 includes a web-based function. As discussed in more detail below, in one embodiment, database 170 is a patient need profile database under the control of, or otherwise accessible by, a process for providing a healthcare expense donation network, and/or a healthcare management system and/or a computing system implemented data management system.

In one embodiment, patient need profile data and/or financial data associated with one or more healthcare consumers, and/or process for providing a healthcare expense donation network 200, and/or one or more healthcare management systems, and/or one or more computing system implemented data management systems, is stored, in whole, or in part, in database 170, and is used by, or is accessed by, process for providing a healthcare expense donation network 200. In one embodiment, database 170 is accessible by one or more users. In one embodiment, database 170 is used, and/or accessible, by a computing system, such as computing systems 100, 120, 140, and/or 150.

In one embodiment, computing systems 100, 140, and 150, and database 170, are coupled to a process provider computing system 120 through network 130. In one embodiment, process provider computing system 120 includes a display device 125, a processor 121, a memory 123, and a network interface 122.

In one embodiment, memory 123 includes all, or part, of a healthcare management system 126, such as any healthcare management system defined herein, known in the art at the time of filing, and/or as developed thereafter. In one embodiment, healthcare management system 126 is stored, in whole, or in part, in memory system 123, and is used by, or includes, or is accessed by, and/or is otherwise associated with process for providing a healthcare expense donation network 200 and/or one or more healthcare consumers, i.e., the given healthcare consumer and/or any healthcare consumers other than the given healthcare consumer.

In one embodiment, process provider computing system 120 is an application server for providing all, or part of process for providing a healthcare expense donation network 200 to one or more of, donor computing system 150, healthcare service provider computing system 140, and database 170.

In one embodiment, process provider computing system 120 collects patient need profile data from one or more healthcare consumers, verifies the patient need profile data, transforms the patient need profile data into patient need profiles, and then distributes one or more of the patient need profiles to one or more donors. In one embodiment, process provider computing system 120 also facilitates a payments means whereby the funds donated by a donor are transferred to the healthcare service provider owed the funds.

In one embodiment, process provider computing system 120 is used in a station-to-station arrangement, such as a peer-to-peer, or hybrid peer-to peer, arrangement, as an indexing and/or central server used to connect a first computing system, such as healthcare consumer computing system 100, and a second computing system, such as computing system 150 or 140.

In one embodiment, data associated with one or more healthcare consumers, and/or process for providing a healthcare expense donation network 200, and/or one or more healthcare management systems, and/or one or more computing system implemented data management systems, is stored, in whole, or in part, in process provider computing system 120, and is used by, or is accessed by, process for providing a healthcare expense donation network 200. In one embodiment, process provider computing system 120 is accessible by one or more users. In one embodiment, process provider computing system 120 is used, and/or accessible, by a computing system, such as computing systems 100, 140, and/or 150, and/or one or more databases, such as database 170.

Network 130 can be any network or network system as discussed herein, and/or known in the art at the time of filing, and/or as developed after the time of filing, capable of allowing communication between two or more computing systems, server systems, and/or databases.

In one embodiment, computing systems 100, 120, 140, and 150, and database 170, are part of a cloud computing environment.

Those of skill in the art will readily recognize that the components shown in FIG. 1, such as computing systems 100, 120, 140, 150 and database 170, and their respective components, are shown for illustrative purposes only and that architectures with more or fewer components can implement, and benefit from, a process for providing a healthcare expense donation network, such as exemplary process for providing a healthcare expense donation network 200 discussed below. Moreover, one or more components of computing systems 100, 120, 140, 150 and database 170, and their respective components may be located remotely from their respective system and accessed via network, as discussed herein. In addition, the particular type of, and configuration of, computing systems 100, 120, 140, 150 and database 170, and their respective components are not relevant.

In various embodiments, all, or part, of one or more components of computing systems 100, 120, 140, 150 and database 170, and their respective components may be associated in a cloud computing environment.

As discussed in more detail below, in one embodiment, a process for providing a healthcare expense donation network, and/or one or more computing system implemented processes, is/are stored in whole, or in part, in one or more memory systems, and/or cache memories, associated with one or more computing systems, such as computing systems 100, 120, 140, 150 and executed on another computing system. As used herein, a memory refers to a volatile memory, a non-volatile memory, or any combination of the two.

Although a process for providing a healthcare expense donation network, and/or one or more computing system implemented processes, can sometimes be referred to herein, alternatively, as a process, an application, a module, a program, a component of a software system, a component of a software package, a component of a parent system, or a feature of a parent system, this terminology is illustrative only. In some embodiments, a process for providing a healthcare expense donation network, and/or one or more computing system implemented processes, is/are capable of being called from an application or the operating system. In one embodiment, an application or program is generally defined to be any executable code. Moreover, those of skill in the art will understand that when it is said that an application or an operation takes some action, the action is the result of executing one or more instructions by a processor, such as CPUs 101, 121, 141, and/or 151. In one embodiment, execution of a process for providing a healthcare expense donation network, and/or one or more computing system implemented processes, by CPUs 101, 121, 141, and/or 151, results in the operations of an agent computer process (not shown) and/or a rule computer process (not shown).

In one embodiment, a process for providing a healthcare expense donation network, and/or one or more computing system implemented processes, is/are a computer application or process implemented and/or run and/or stored, in full, or in part, in, or on, a computer program product. Herein, a computer program product comprises a medium configured to store and/or transport computer readable code, whether known at the time of filing or as later developed. Some examples of computer program products are CD-ROM discs, DVDs, ROM cards, floppy discs, magnetic tapes, computer hard drives, servers on a network, or other media or process capable of delivering computer readable data representing computer readable code, whether known at the time of filing or as later developed. This medium may belong to a computing system, such as computing systems 100, 102, 140 and/or 150, of FIG. 1, described above. However, the medium also may be removed from the computing system.

For example, all, or part, of a process for providing a healthcare expense donation network, and/or one or more computing system implemented processes, may be stored in a memory that is physically located in a location, such as database 170 of FIG. 1, different from a computing system, such as computing systems 100, 102, 140 and/or 150, of FIG. 1, utilizing process for providing a healthcare expense donation network 200, and/or one or more computing system implemented processes. In one embodiment, all, or part, of process for providing a healthcare expense donation network 200, and/or one or more computing system implemented processes, may be stored in a memory that is physically located, separate from the computing system's processor(s), and the computing system processor(s) can be coupled to the memory in a client-server system, or, alternatively, via connection to another computer, via modems and analog lines, digital interfaces and a digital carrier line, or wireless or cellular connections.

In one embodiment, the computing system and/or server system, such as computing systems 100, 102, 140 and/or 150, running and/or utilizing and/or storing all, or part, of process for providing a healthcare expense donation network 200, and/or one or more computing system implemented processes, is a portable computer, a workstation, a two-way pager, a cellular telephone, a smart phone, a digital wireless telephone, a personal digital assistant, a server computer, an Internet appliance, or any other device that includes components that can execute all, or part, of process for providing a healthcare expense donation network 200, and/or one or more computing system implemented processes, in accordance with at least one of the embodiments as described herein. Similarly, in another embodiment, process for providing a healthcare expense donation network 200, and/or one or more computing system implemented processes, is/are implemented on and/or run and/or stored on a computing system and/or server system that is comprised of multiple different computers, wireless devices, cellular telephones, digital telephones, two-way pagers, personal digital assistants, server computers, or any desired combination of these devices, that are interconnected to perform the processes as described herein.

Process

Herein, the term "patient" includes any party who has received and/or may be receiving healthcare services for which a healthcare consumer, who my in some cases may be the patient, is financially responsible.

Herein, the term "healthcare consumer", includes any person/party who is financially responsible for making healthcare service payments associated with one or more patients. In some cases, the healthcare consumer and the patient are the same party/person.

Herein, the terms "healthcare" and "healthcare services" are used interchangeably and include any general and/or specialized treatment, assessment, maintenance, therapy, medication, and/or advice relating to all, or any portion of, a user healthcare consumer's state of health, including but not limited to: general medical, specialized medical, surgical, dental, vision, psychological, and/or any other type of treatment, assessment, maintenance, therapy, medication, and/or advice.

Herein, the term "healthcare benefit plan" and "health insurance plan" are used interchangeably to denote any policy, program, means and/or mechanism whereby a user healthcare consumer is provided benefits and/or service and/or entitlements to healthcare.

Herein, the terms "healthcare benefit plan provider", "healthcare benefit plan sponsor", "employer" and/or "organization" are used to denote any individual party, organization, or group that provides, presents, offers, pays for, in whole or in part, or is otherwise associated with giving a user healthcare consumer access to one or more healthcare benefit plans, health insurance, and/or healthcare expense account programs.

As used herein, the term "computing system", includes, but is not limited to: a desktop computer; a portable computer; a workstation; a two-way pager; a cellular telephone; a smart phone; a digital wireless telephone; a Personal Digital Assistant (PDA); a media player, i.e., an MP3 player and/or other music and/or video player; a server computer; an Internet appliance; or any other device that includes components that can execute all, or part, of any one of the processes and/or operations as described herein. In addition, as used herein, the term computing system, can denote, but is not limited to, computing systems made up of multiple: computers; wireless devices; cellular telephones; digital telephones; two-way pagers; PDAs; media players; server computers; or any desired combination of these devices, that are coupled to perform the processes and/or operations as described herein.

As used herein, the term "computing system implemented data management system" includes, but is not limited to:

computing system implemented accounting and/or invoicing systems, packages, programs, modules, or applications; financial management systems, packages, programs, modules, or applications; financial management systems, packages, programs, modules, or applications; computing system implemented banking systems, packages, programs, modules, or applications; computing system implemented personal and small business financial management systems, packages, programs, modules, or applications; computing system implemented business systems, packages, programs, modules, or applications; computing system implemented marketing device distribution systems, packages, programs, modules, or applications; computing system implemented financial institution financial management systems, packages, programs, modules, or applications; computing system implemented tax preparation systems, packages, programs, modules, or applications; computing system implemented business and/or point of sale systems, packages, programs, modules, or applications; computing system implemented healthcare management systems, packages, programs, modules, or applications and various other electronic data driven data management systems, packages, programs, modules, or applications, whether known at the time of filling or as developed later.

As used herein, the term "network" includes, but is not limited to, any network or network system such as, but not limited to, a peer-to-peer network, a hybrid peer-to-peer network, a Local Area Network (LAN), a Wide Area Network (WAN), a public network, such as the Internet, a private network, a cellular network, a combination of different network types, or other wireless, wired, and/or a wireless and wired combination network capable of allowing communication between two or more computing systems, whether available or known at the time of filing or as later developed.

As used herein, the term "database" includes, but is not limited to, any data storage mechanism known at the time of filing or as developed thereafter, such as, but not limited to: a data storage device; a designated server system or computing system, or a designated portion of one or more server systems or computing systems; a mobile computing system; a server system network; a distributed database; or an external and/or portable hard drive. Herein, the term "database" can refer to a dedicated mass storage device implemented in software, hardware, or a combination of hardware and software. Herein, the term "database" can refer to a web-based function. Herein, the term "database" can refer to any data storage means that is part of, or under the control of, any computing system, as discussed herein, known at the time of filing, or as developed thereafter.

In accordance with one embodiment, a method and system for providing a healthcare expense donation network includes a process for providing a healthcare expense donation network whereby, in one embodiment, a third party provided healthcare management system, such as a computing system or on-line implemented healthcare expense tacking and/or payment system, provides a service through which a healthcare consumer can create a patient need profile indicating a need for help in paying their healthcare expenses and requesting donations to this end. In one embodiment, the healthcare consumer's healthcare expenses are verified, as well as any other financial and/or personal data associated with the submitted patient need profile that potential donors, the patients, and/or the provider of the process for providing a healthcare expense donation network desires to be verified. In one embodiment, once the healthcare consumer's healthcare expenses, and/or other patient need profile data, are verified, the patient need profile is made available to potential donors including, but not limited to: the healthcare service provider to whom the funds are owed; potential donors designated by the healthcare consumer, such as family and friends; pre-registered potential donors that have indicated a desire to help specific verified types of patients and/or healthcare consumers with verified healthcare expense needs; pre-registered potential donors who have indicated a desire to help any verified patients and/or healthcare consumers with any verified healthcare expense needs; and/or various other potential donor parties and/or organizations associated with specific types of patients/healthcare needs or general patient/healthcare assistance. In one embodiment, the potential donors are provided the ability to securely make donations to the patient's healthcare expenses directly, in one embodiment, through the notification of need and attached patient need profile. In one embodiment, any funds so contributed by a donor are forwarded directly to the healthcare provider to whom the money is owed and the patient is informed of the deposited funds and any remaining balance. In one embodiment, an updated balance of funds owed is included in the patient need profile. In one embodiment, any donors making a donation are provided documentation data indicating the donation, the remaining balance, and any data required for tax purposes.

Figure 2:
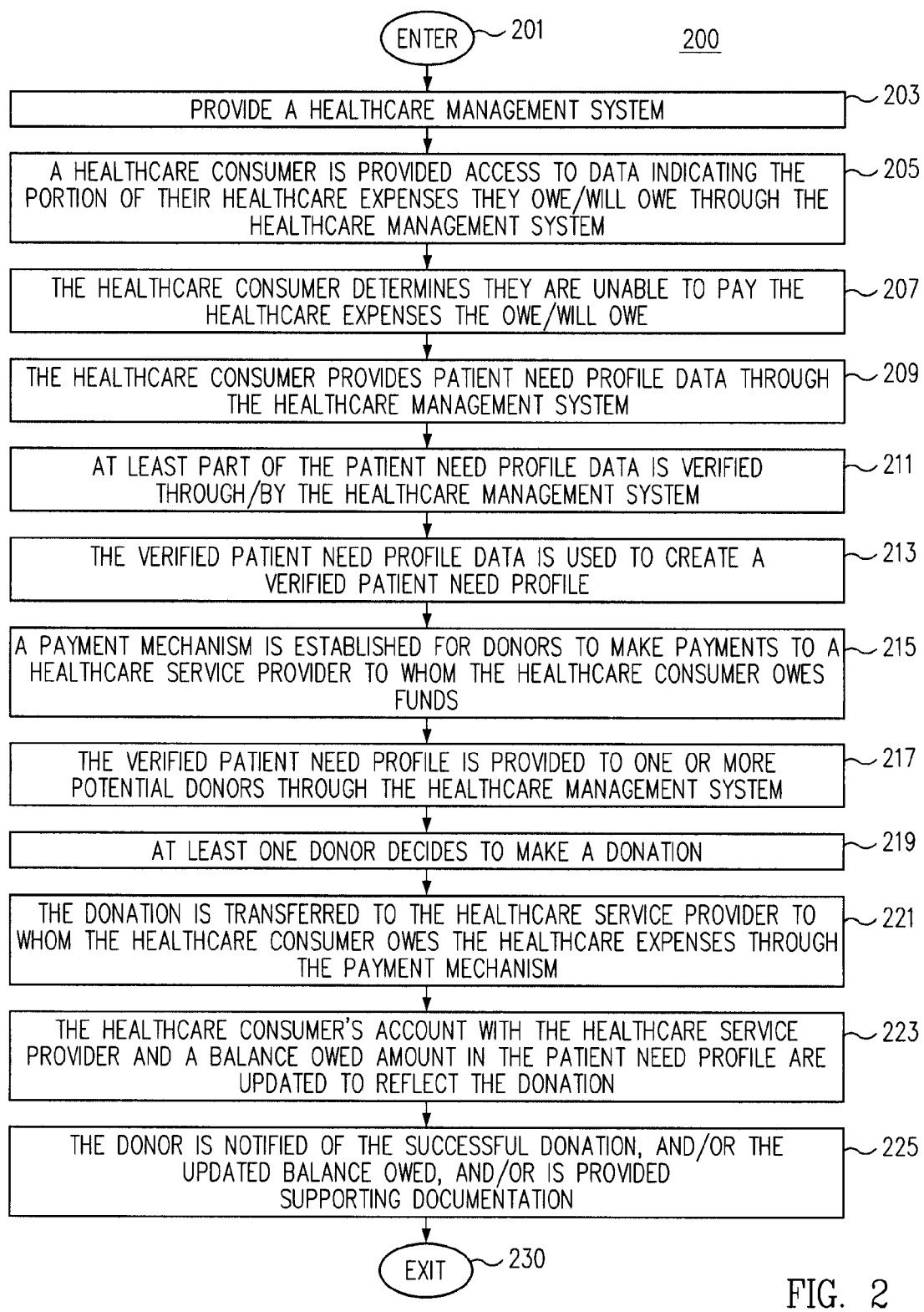
FIG. 2 is a flow chart depicting a process for providing a healthcare expense donation network in accordance with one embodiment.

FIG. 2 a flow chart depicting a process for providing a healthcare expense donation network 200 in accordance with one embodiment. Process for providing a healthcare expense donation network 200 begins at ENTER OPERATION 201 of FIG. 2 and process flow proceeds to PROVIDE A HEALTHCARE MANAGEMENT SYSTEM OPERATION 203.

In one embodiment, at PROVIDE A HEALTHCARE MANAGEMENT SYSTEM OPERATION 203 a healthcare management system is provided to a healthcare consumer.

In one embodiment, at PROVIDE A HEALTHCARE MANAGEMENT SYSTEM OPERATION 203 the healthcare management system is provided by a healthcare management system provider such as any computing system and/or on-line healthcare management system, as defined herein, known in the art at the time of filing, and/or as developed thereafter.

In one embodiment, at PROVIDE A HEALTHCARE MANAGEMENT SYSTEM OPERATION 203 a healthcare management system, such as healthcare management system 180 and/or 126 of FIG. 1, is provided to a healthcare consumer via a healthcare consumer computing system, such as healthcare consumer computing system 100 of FIG. 1, by a healthcare management system provider via an application server or website server, such as provider computing system 120 of FIG. 1.

Returning to FIG. 2, and as noted above, herein the term healthcare management system includes, but is not limited to a computing system and/or on-line implemented system that helps a user healthcare consumer track their healthcare expenses by gathering healthcare expense data from one or more sources, such as invoices, EOBs, and financial transaction records, and then organizing, categorizing, and/or displaying the data in one or more summary displays and/or reports.

Specific examples of currently available healthcare management systems include, but are not limited to: Quicken Health Expense Tracker™, available from Intuit Inc. of Mountain View, Calif.; Intuit Health Bill Pay™ available from Intuit Inc. of Mountain View, Calif.; and/or any other computing system implemented and/or on-line healthcare management applications, programs, or systems, as discussed herein, and or as known in the art at the time of filing, and/or as developed after the time of filing.

In one embodiment, at PROVIDE A HEALTHCARE MANAGEMENT SYSTEM OPERATION 203 the healthcare management system is provided by a healthcare management system provider who is a third party, i.e., is neither the healthcare consumer nor the healthcare service provider.

In one embodiment, at PROVIDE A HEALTHCARE MANAGEMENT SYSTEM OPERATION 203 the healthcare management system is provided by a healthcare management system provider who is also the provider of at least part of process for providing a healthcare expense donation network 200.

In one embodiment, once a healthcare management system is provided to a healthcare consumer at PROVIDE A HEALTHCARE MANAGEMENT SYSTEM OPERATION 203 process flow proceeds to A HEALTHCARE CONSUMER IS PROVIDED ACCESS TO DATA INDICATING THE PORTION OF THEIR HEALTHCARE EXPENSES THEY OWE/WILL OWE THROUGH THE HEALTHCARE MANAGEMENT SYSTEM OPERATION 205.

In one embodiment, at A HEALTHCARE CONSUMER IS PROVIDED ACCESS TO DATA INDICATING THE PORTION OF THEIR HEALTHCARE EXPENSES THEY OWE/WILL OWE THROUGH THE HEALTHCARE MANAGEMENT SYSTEM OPERATION 205, the healthcare consumer is provided access to the healthcare management system of PROVIDE A HEALTHCARE MANAGEMENT SYSTEM OPERATION 203 and data indicating current or estimated healthcare services fees owed/to be owed for healthcare services provided to a patient associated with the healthcare consumer.

As noted above, in one embodiment, at A HEALTHCARE CONSUMER IS PROVIDED ACCESS TO DATA INDICATING THE PORTION OF THEIR HEALTHCARE EXPENSES THEY OWE/WILL OWE THROUGH THE HEALTHCARE MANAGEMENT SYSTEM OPERATION 205, the healthcare consumer is provided access to the healthcare management system, such as healthcare management system 180 and/or 126 of FIG. 1, of PROVIDE A HEALTHCARE MANAGEMENT SYSTEM OPERATION 203 via a healthcare consumer computing system, such as healthcare consumer computing system 100 of FIG. 1, by a healthcare management system provider via an application server or website server, such as provider computing system 120 of FIG. 1.

In one embodiment, at A HEALTHCARE CONSUMER IS PROVIDED ACCESS TO DATA INDICATING THE PORTION OF THEIR HEALTHCARE EXPENSES THEY OWE/WILL OWE THROUGH THE HEALTHCARE MANAGEMENT SYSTEM OPERATION 205, the healthcare consumer is provided access to data indicating current or estimated healthcare services fees owed/to be owed for healthcare services provided to a patient associated with the healthcare consumer obtained, estimated, and/or aggregated by the healthcare management system into one or more summaries of data and/or reports viewable by the healthcare consumer.

In one embodiment, at A HEALTHCARE CONSUMER IS PROVIDED ACCESS TO DATA INDICATING THE PORTION OF THEIR HEALTHCARE EXPENSES THEY OWE/WILL OWE THROUGH THE HEALTHCARE MANAGEMENT SYSTEM OPERATION 205 the healthcare consumer views data indicating current or estimated healthcare services fees owed/to be owed for healthcare services provided to a patient associated with the healthcare consumer obtained from invoices, EOB data, healthcare benefit plan providers, or any other source of actual and/or estimated healthcare service fees owed/to be owed by the healthcare service consumer after any healthcare benefit plans have paid their share, i.e. the healthcare consumer's "out-of-pocket" costs.

In one embodiment, once the healthcare consumer is provided access to the healthcare management system of PROVIDE A HEALTHCARE MANAGEMENT SYSTEM OPERATION 203 and data indicating current or estimated healthcare services fees owed/to be owed for healthcare services provided to a patient associated with the healthcare consumer at A HEALTHCARE CONSUMER IS PROVIDED ACCESS TO DATA INDICATING THE PORTION OF THEIR HEALTHCARE EXPENSES THEY OWE/WILL OWE THROUGH THE HEALTHCARE MANAGEMENT SYSTEM OPERATION 205 process flow proceeds to THE HEALTHCARE CONSUMER DETERMINES THEY ARE UNABLE TO PAY THE HEALTHCARE EXPENSES THEY OWE/WILL OWE OPERATION 207.

In one embodiment, at THE HEALTHCARE CONSUMER DETERMINES THEY ARE UNABLE TO PAY THE HEALTHCARE EXPENSES THEY OWE/WILL OWE OPERATION 207, after reviewing the data indicating current or estimated healthcare services fees owed/to be owed for healthcare services provided to a patient associated with the healthcare consumer of A HEALTHCARE CONSUMER IS PROVIDED ACCESS TO DATA INDICATING THE PORTION OF THEIR HEALTHCARE EXPENSES THEY OWE/WILL OWE THROUGH THE HEALTHCARE MANAGEMENT SYSTEM OPERATION 205, the healthcare consumer determines that they cannot afford to pay all, or part of, the healthcare services fees owed/to be owed and desire assistance for paying the healthcare expenses.

In one embodiment, once the healthcare consumer determines that they cannot afford to pay all, or part of, the healthcare services fees owed/to be owed and desire assistance for paying the healthcare expenses at THE HEALTHCARE CONSUMER DETERMINES THEY ARE UNABLE TO PAY THE HEALTHCARE EXPENSES THEY OWE/WILL OWE OPERATION 207, process flow proceeds to THE HEALTHCARE CONSUMER PROVIDES PATIENT NEED PROFILE DATA THROUGH THE HEALTHCARE MANAGEMENT SYSTEM OPERATION 209.

In one embodiment, at THE HEALTHCARE CONSUMER PROVIDES PATIENT NEED PROFILE DATA THROUGH THE HEALTHCARE MANAGEMENT SYSTEM OPERATION 209 the healthcare consumer provides patient need profile data to the healthcare management system of PROVIDE A HEALTHCARE MANAGEMENT SYSTEM OPERATION 203.

In one embodiment, at THE HEALTHCARE CONSUMER PROVIDES PATIENT NEED PROFILE DATA THROUGH THE HEALTHCARE MANAGEMENT SYSTEM OPERATION 209 the healthcare consumer is provided a link through the healthcare management system to a patient need profile data entry screen.

In one embodiment, at THE HEALTHCARE CONSUMER PROVIDES PATIENT NEED PROFILE DATA THROUGH THE HEALTHCARE MANAGEMENT SYSTEM OPERATION 209 the healthcare consumer is provided the patient need profile data entry screen via a display device, such as display device 115, of a healthcare consumer computing system, such as healthcare consumer computing system 100, of FIG. 1.

Returning to FIG. 2, in one embodiment, the patient need profile data entry screen requests various patient need profile data from the healthcare consumer such as, but not limited to, any one or more of: the patient's name, age, DOB, demographic data, etc.; the patient's illness/injury associated with the healthcare service expenses owed; the providers of the healthcare services for which funds are owed; images of the patient, the patient's family and/or the healthcare consumer; how much the healthcare consumer has already paid; how much is owed; any healthcare benefit plans associated with the patient/healthcare consumer; biographical and/or historical information associated with the healthcare consumer, the patient, the family, etc.; financial data associated with the healthcare consumer, such as income, savings, assets, etc.; contact data, e-mail, phone, address, etc., associated with any potential donors known by the healthcare consumer, such as family and friends; data granting the process for providing a healthcare expense donation network, a provider of the process for providing a healthcare expense donation network, or any other party associated with the process for providing a healthcare expense donation network, permission to obtain and/or verify any of the patient need profile data provided by the healthcare consumer from any party or source; and/or any other data desired by the patient, the healthcare consumer, potential donors, and/or the healthcare management system provider.

In one embodiment, the healthcare consumer provides the patient need profile data via a patient need profile data entry screen and a user interface device, such as a keyboard, mouse, touch pad, voice recognition software, or any other means and/or mechanism for converting user actions into computing system processes, as discussed herein, and/or as known in the art at the time of filing, and/or as developed after the time of filing.

In one embodiment, at THE HEALTHCARE CONSUMER PROVIDES PATIENT NEED PROFILE DATA THROUGH THE HEALTHCARE MANAGEMENT SYSTEM OPERATION 209 the healthcare consumer submits the patient need profile data to the healthcare management system provider through the patient need profile data entry screen and/or the healthcare management system by any means, method, process, or procedure as discussed herein, and/or as known in the art at the time of filing, and/or as developed after the time of filing.

In one embodiment, once the healthcare consumer provides patient need profile data to the healthcare management system of PROVIDE A HEALTHCARE MANAGEMENT SYSTEM OPERATION 203 at THE HEALTHCARE CONSUMER PROVIDES PATIENT NEED PROFILE DATA THROUGH THE HEALTHCARE MANAGEMENT SYSTEM OPERATION 209, process flow proceeds to AT LEAST PART OF THE PATIENT NEED PROFILE DATA IS VERIFIED THROUGH/BY THE HEALTHCARE MANAGEMENT SYSTEM OPERATION 211.

In one embodiment, at AT LEAST PART OF THE PATIENT NEED PROFILE DATA IS VERIFIED THROUGH/BY THE HEALTHCARE MANAGEMENT SYSTEM OPERATION 211 at least part of the patient need profile data of THE HEALTHCARE CONSUMER PROVIDES PATIENT NEED PROFILE DATA THROUGH THE HEALTHCARE MANAGEMENT SYSTEM OPERATION 209 is verified by the healthcare management system and/or healthcare management system provider of PROVIDE A HEALTHCARE MANAGEMENT SYSTEM OPERATION 203.

In one embodiment, at AT LEAST PART OF THE PATIENT NEED PROFILE DATA IS VERIFIED THROUGH/BY THE HEALTHCARE MANAGEMENT SYSTEM OPERATION 211 at least part of the patient need profile data is verified by the healthcare management system and/or healthcare management system provider by contacting the healthcare service provider owed the funds and/or any healthcare benefit plan providers involved.

As noted above, in some embodiments, the healthcare management system, helps a user healthcare consumer track their healthcare expenses by gathering healthcare expense data from one or more sources, such as invoices, EOBs, and financial transaction records, and then organizing, categorizing, and/or displaying the data in one or more summary displays and/or reports. Consequently, in some embodiments, the healthcare management system and/or healthcare management system provider already have access to at least part of the healthcare consumer's data.

In addition, in some instances, the healthcare management system and/or the process for providing a healthcare expense donation network is associated with one or more other data management systems, such as, but not limited to: computing system implemented accounting and/or invoicing systems, packages, programs, modules, or applications; personal financial management systems, packages, programs, modules, or applications; financial management systems, packages, programs, modules, or applications; computing system implemented banking systems, packages, programs, modules, or applications; computing system implemented personal and small business financial management systems, packages, programs, modules, or applications; computing system implemented business systems, packages, programs, modules, or applications; computing system implemented marketing device distribution systems, packages, programs, modules, or applications; computing system implemented financial institution financial management systems, packages, programs, modules, or applications; computing system implemented tax preparation systems, packages, programs, modules, or applications; computing system implemented business and/or point of sale systems, packages, programs, modules, or applications; computing system implemented healthcare management systems, packages, programs, modules, or applications and various other electronic data driven data management systems, packages, programs, modules, or applications, whether known at the time of filling or as developed later. Consequently, in some embodiments, the healthcare management system and/or healthcare management system provider can readily obtain access to at least part of the healthcare consumer's data, including the general financial data associated with the healthcare consumer, to verify that the healthcare consumer not only has genuine and verified healthcare expenses, but also has a genuine and verified financial need.

For instance, as noted above, in one embodiment, process for providing a healthcare expense donation network 200 is part of a parent healthcare management, such as healthcare management systems 180 and/or 126 of FIG. 1, and/or a personal financial, business financial, accounting, or tax preparation software system, program, package or application, that implements, includes, is accessed by, and/or is otherwise associated with process for providing a healthcare expense donation network 200 (FIG. 2). In these embodiments, the patient need profile data may be obtained directly from, or through, the parent computing system implemented software system, program, package or application, such as healthcare management system 180 of FIG. 1.

Returning to FIG. 2, in one embodiment, the patient need profile data is obtained from invoices/patient bills and/or claim data provided to process for providing a healthcare expense donation network 200, and or a parent computing system implemented process, by healthcare providers such as hospitals and/or doctors and/or other medical service personnel.

As discussed above, in one embodiment, process for providing a healthcare expense donation network 200 is part of a parent healthcare management, such as healthcare management systems 180 and/or 126 of FIG. 1, and/or a personal financial, business financial, accounting, or tax preparation software system, program, package or application, that implements, includes, is accessed by, and/or is otherwise associated with process for providing a healthcare expense donation network 200 (FIG. 2) as one of multiple features. Some of these parent systems provide the capability to obtain, receive, and/or process electronic copies of the invoices/claims, often in their specific formats, and then store the data for use by process for providing a healthcare expense donation network 200 in one of numerous locations by one of numerous methods known to those of skill in the art.

In one embodiment, the patient need profile data is obtained from Explanation of Benefits (EOB) data provided to process for providing a healthcare expense donation network 200 by a health insurance provider and/or the user healthcare consumer.

According to one embodiment, the health insurance providers transfer electronic copies of the EOBs, often in specific formats, to the provider of process for providing a healthcare expense donation network 200, and or a parent computing system implemented process. As discussed above, in one embodiment, process for providing a healthcare expense donation network 200 is part of a parent healthcare management, such as healthcare management systems 180 and/or 126 of FIG. 1, and/or a personal financial, business financial, accounting, or tax preparation software system, program, package or application, that implements, includes, is accessed by, and/or is otherwise associated with process for providing a healthcare expense donation network 200 (FIG. 2). Some of these parent systems provide the capability to obtain, receive, and/or process electronic copies of the EOBs and then store the data for use by process for providing a healthcare expense donation network 200 in one of numerous locations by one of numerous methods known to those of skill in the art.

In one embodiment, the patient need profile data is obtained from one or more of the following: a healthcare management system/application; a healthcare management web-site; a healthcare financial management system/application; a healthcare financial management web-site; a health information system/application; a health information web-site; a health insurance system/application; and/or a health insurance web-site.

In various embodiments, at AT LEAST PART OF THE PATIENT NEED PROFILE DATA IS VERIFIED THROUGH/BY THE HEALTHCARE MANAGEMENT SYSTEM OPERATION 211 at least part of the patient need profile data is verified by the healthcare management system and/or healthcare management system provider using any data verification means, procedure, process, and/or source, as discussed herein, and/or as known in the art at the time of filing, and/or as developed after the time of filing.

In one embodiment, once at least part of the patient need profile data of THE HEALTHCARE CONSUMER PROVIDES PATIENT NEED PROFILE DATA THROUGH THE HEALTHCARE MANAGEMENT SYSTEM OPERATION 209 is verified by the healthcare management system and/or healthcare management system provider of PROVIDE A HEALTHCARE MANAGEMENT SYSTEM OPERATION 203 at AT LEAST PART OF THE PATIENT NEED PROFILE DATA IS VERIFIED THROUGH/BY THE HEALTHCARE MANAGEMENT SYSTEM OPERATION 211, process flow proceeds to THE VERIFIED PATIENT NEED PROFILE DATA IS USED TO CREATE A VERIFIED PATIENT NEED PROFILE OPERATION 213.

In one embodiment, at THE VERIFIED PATIENT NEED PROFILE DATA IS USED TO CREATE A VERIFIED PATIENT NEED PROFILE OPERATION 213 at least part of the patient need profile data, and the verified patient need profile data of AT LEAST PART OF THE PATIENT NEED PROFILE DATA IS VERIFIED THROUGH/BY THE HEALTHCARE MANAGEMENT SYSTEM OPERATION 211, is processed by one or more processors, such as CPUs 101, 151, 141, and/or 121, associated with one or more computing systems, such as computing systems 100, 120, 140 and/or 150 of FIG. 1, and transformed into a verified patient need profile.

Returning to FIG. 2, in various embodiments, at THE VERIFIED PATIENT NEED PROFILE DATA IS USED TO CREATE A VERIFIED PATIENT NEED PROFILE OPERATION 213 the verified patient need profile includes, but is not limited to, any one or more of: data indicating the patient's name, age, DOB, demographic data etc.; data indicating the patient's illness/injury associated with the healthcare service expenses owed; data indicating the providers of the healthcare services for which funds are owed; data indicating biographical and/or historical information associated with the healthcare consumer, the patient, the family, etc.; data indicating the financial need associated with the healthcare consumer, such as income, savings, assets etc. contact data; data indicating which portion of the verified patient need profile data has been verified; data indicating an updated balance of amounts owed; data indicating how much the healthcare consumer has already paid themselves; any images submitted by the healthcare consumer of the patient, patient's family and/or the healthcare consumer; and/or any other data desired by the patient, the healthcare consumer, potential donors, and/or the healthcare management system provider.

In one embodiment, at THE VERIFIED PATIENT NEED PROFILE DATA IS USED TO CREATE A VERIFIED PATIENT NEED PROFILE OPERATION 213, data representing the verified patient need profile is stored by any one of various data storage means and using any data storage mechanism as discussed herein, and/or as known in the art at the time of filing, and/or as developed after the time of filing.

For instance, in one embodiment, at THE VERIFIED PATIENT NEED PROFILE DATA IS USED TO CREATE A VERIFIED PATIENT NEED PROFILE OPERATION 213 the patient need profile data is stored, in whole, or in part, in a database, such as database 170 of FIG. 1, maintained by, accessible by, owned by, or otherwise related to, a provider of process for providing a healthcare expense donation network 200 by any one of the numerous mechanisms known to those of skill in the art. In other instances, the data, in whole, or in part, is stored in a memory system, such as memory systems 103, 123, 143, or 153, or another database, of FIG. 1, or in a cache memory, such as cache memory 103A, 143A, 153A of FIG. 1, or in any main memory or mass memory, associated with any computing system described above. In one embodiment, the data, in whole, or in part, is stored in any location, or on/in a computer readable medium, and/or any other computer program product, as defined herein. In one embodiment, the data, in whole, or in part, is stored on a webpage, in a web-based system or on a public network such as the Internet.

Returning to FIG. 2, in some embodiments, at THE VERIFIED PATIENT NEED PROFILE DATA IS USED TO CREATE A VERIFIED PATIENT NEED PROFILE OPERATION 213 the data stored as described above is maintained, in whole, or in part, by: the provider of process for providing a healthcare expense donation network 200; a health insurance provider; a healthcare service provider; a third party data storage institution; any third party service or institution; or any other parties.

In one embodiment, at THE VERIFIED PATIENT NEED PROFILE DATA IS USED TO CREATE A VERIFIED PATIENT NEED PROFILE OPERATION 213 the healthcare consumer's healthcare expenses are verified, as well as any other financial and/or personal data associated with the submitted patient need profile that potential donors, the patients, and/or the provider of the process for providing a healthcare expense donation network desires to be verified.

In one embodiment, once at least part of the patient need profile data, and the verified patient need profile data of AT LEAST PART OF THE PATIENT NEED PROFILE DATA IS VERIFIED THROUGH/BY THE HEALTHCARE MANAGEMENT SYSTEM OPERATION 211, is processed by one or more processors, and transformed into a verified patient need profile at THE VERIFIED PATIENT NEED PROFILE DATA IS USED TO CREATE A VERIFIED PATIENT NEED PROFILE OPERATION 213, process flow proceeds to A PAYMENT MECHANISM IS ESTABLISHED FOR DONORS TO MAKE PAYMENTS TO A HEALTHCARE SERVICE PROVIDER TO WHOM THE HEALTHCARE CONSUMER OWES FUNDS OPERATION 215.

In one embodiment, at A PAYMENT MECHANISM IS ESTABLISHED FOR DONORS TO MAKE PAYMENTS TO A HEALTHCARE SERVICE PROVIDER TO WHOM THE HEALTHCARE CONSUMER OWES FUNDS OPERATION 215 one or more payment mechanisms are established by, and/or through, the healthcare management system and/or healthcare management system provider.

In one embodiment, the one or more payment mechanisms are established at A PAYMENT MECHANISM IS ESTABLISHED FOR DONORS TO MAKE PAYMENTS TO A HEALTHCARE SERVICE PROVIDER TO WHOM THE HEALTHCARE CONSUMER OWES FUNDS OPERATION 215 to provide a potential donor a means for making a payment to a healthcare service provider to whom the healthcare consumer owes the funds on behalf of the healthcare consumer, and through the healthcare management system and/or a provided verified patient need profile, without having to access any other site or contact any other third party, i.e., through a single, and in one embodiment, secure, interface and/or transaction.

In one embodiment, the one or more payment mechanisms established by, and/or through, the healthcare management system and/or healthcare management system provider of A PAYMENT MECHANISM IS ESTABLISHED FOR DONORS TO MAKE PAYMENTS TO A HEALTHCARE SERVICE PROVIDER TO WHOM THE HEALTHCARE CONSUMER OWES FUNDS OPERATION 215 include, but are not limited to, setting up a merchant account for the healthcare service provider, in one embodiment through the healthcare management system, that is linked with the healthcare service provider's bank account to route the payments directly to the healthcare service provider after a payment is made.

In one embodiment, the one or more payment mechanisms established by, and/or through, the healthcare management system and/or healthcare management system provider of A PAYMENT MECHANISM IS ESTABLISHED FOR DONORS TO MAKE PAYMENTS TO A HEALTHCARE SERVICE PROVIDER TO WHOM THE HEALTHCARE CONSUMER OWES FUNDS OPERATION 215 include, but are not limited to, setting up a patient/healthcare consumer account for the healthcare service provider, in one embodiment through the healthcare management system, and then transferring the funds to the healthcare service provider, in one embodiment through the healthcare management system.

In one embodiment, the one or more payment mechanisms established by, and/or through, the healthcare management system and/or healthcare management system provider of A PAYMENT MECHANISM IS ESTABLISHED FOR DONORS TO MAKE PAYMENTS TO A HEALTHCARE SERVICE PROVIDER TO WHOM THE HEALTHCARE CONSUMER OWES FUNDS OPERATION 215 include, but are not limited to, the healthcare management system and/or healthcare management system provider acting in the role of clearing house to ensure that various donations by various donors made on behalf of various healthcare consumers are transferred to the respective healthcare service providers.

In one embodiment, once one or more payment mechanisms are established by, and/or through, the healthcare management system and/or healthcare management system provider at A PAYMENT MECHANISM IS ESTABLISHED FOR DONORS TO MAKE PAYMENTS TO A HEALTHCARE SERVICE PROVIDER TO WHOM THE HEALTHCARE CONSUMER OWES FUNDS OPERATION 215, process flow proceeds to THE VERIFIED PATIENT NEED PROFILE IS PROVIDED TO ONE OR MORE POTENTIAL DONORS THROUGH THE HEALTHCARE MANAGEMENT SYSTEM OPERATION 217.

In one embodiment, at THE VERIFIED PATIENT NEED PROFILE IS PROVIDED TO ONE OR MORE POTENTIAL DONORS THROUGH THE HEALTHCARE MANAGEMENT SYSTEM OPERATION 217 the verified patient need profile of THE VERIFIED PATIENT NEED PROFILE DATA IS USED TO CREATE A VERIFIED PATIENT NEED PROFILE OPERATION 213 is made available to potential donors including, but not limited to: the healthcare service provider to whom the funds are owed; potential donors designated by the healthcare consumer, such as family and friends; pre-registered potential donors that have indicated a desire to help specific verified types of patients and/or healthcare consumers with verified healthcare expense needs; pre-registered potential donors who have indicated a desire to help any verified patients and/or healthcare consumers with any verified healthcare expense needs; and/or various other potential donor parties and/or organizations associated with specific types of patients/healthcare needs or general patient/healthcare assistance.

In one embodiment, at THE VERIFIED PATIENT NEED PROFILE IS PROVIDED TO ONE OR MORE POTENTIAL DONORS THROUGH THE HEALTHCARE MANAGEMENT SYSTEM OPERATION 217 the verified patient need profile is provided to one or more potential donors through the healthcare management system and/or healthcare management system provider.

In one embodiment, at THE VERIFIED PATIENT NEED PROFILE IS PROVIDED TO ONE OR MORE POTENTIAL DONORS THROUGH THE HEALTHCARE MANAGEMENT SYSTEM OPERATION 217 the verified patient need profile is provided to the healthcare service provider to whom the healthcare consumer owes the funds to provide the healthcare service provider the opportunity to publicly, or privately, discount the amount owed; thereby acting in the role of a donor. In one embodiment, any discount afforded the healthcare consumer by the healthcare service provider is shown in the verified patient need profile.

In one embodiment, at THE VERIFIED PATIENT NEED PROFILE IS PROVIDED TO ONE OR MORE POTENTIAL DONORS THROUGH THE HEALTHCARE MANAGEMENT SYSTEM OPERATION 217 the healthcare service provider sees a request to approve a healthcare consumer's patient need profile and optionally give a discount off of the original bill amount.

In one embodiment, at THE VERIFIED PATIENT NEED PROFILE IS PROVIDED TO ONE OR MORE POTENTIAL DONORS THROUGH THE HEALTHCARE MANAGEMENT SYSTEM OPERATION 217 the verified patient need profile is provided to any potential donors identified by the healthcare consumer, such as family and friends, in the patient need profile data input screen.

In one embodiment, at THE VERIFIED PATIENT NEED PROFILE IS PROVIDED TO ONE OR MORE POTENTIAL DONORS THROUGH THE HEALTHCARE MANAGEMENT SYSTEM OPERATION 217 the verified patient need profile is provided to any potential donors identified by the healthcare consumer, such as family and friends, in the patient need profile data input screen via specific email addresses and/or via links to social networking sites such as Facebook™ or MySpace™.

In one embodiment, at THE VERIFIED PATIENT NEED PROFILE IS PROVIDED TO ONE OR MORE POTENTIAL DONORS THROUGH THE HEALTHCARE MANAGEMENT SYSTEM OPERATION 217 the verified patient need profile is provided to pre-registered potential donors that have indicated a desire to help specific verified types of patients and/or healthcare consumers with verified healthcare expense needs.

In one embodiment, at THE VERIFIED PATIENT NEED PROFILE IS PROVIDED TO ONE OR MORE POTENTIAL DONORS THROUGH THE HEALTHCARE MANAGEMENT SYSTEM OPERATION 217 the verified patient need profile is provided to pre-registered potential donors who have indicated a desire to help any verified patients and/or healthcare consumers with any verified healthcare expense needs.

In one embodiment, at THE VERIFIED PATIENT NEED PROFILE IS PROVIDED TO ONE OR MORE POTENTIAL DONORS THROUGH THE HEALTHCARE MANAGEMENT SYSTEM OPERATION 217 the verified patient need profile is provided to various other potential donor parties and/or organizations associated with specific types of patients/healthcare needs or general patient/healthcare assistance.

In one embodiment, at THE VERIFIED PATIENT NEED PROFILE IS PROVIDED TO ONE OR MORE POTENTIAL DONORS THROUGH THE HEALTHCARE MANAGEMENT SYSTEM OPERATION 217 the verified patient need profile is provided to one or more potential donors via a network and/or one or more computing systems, such as process provider computing system 120 and/or potential donor computing system 150 of FIG. 1, and/or as known in the art at the time of filing, and/or as developed after the time of filing.

For instance, in one embodiment, at THE VERIFIED PATIENT NEED PROFILE IS PROVIDED TO ONE OR MORE POTENTIAL DONORS THROUGH THE HEALTHCARE MANAGEMENT SYSTEM OPERATION 217 the verified patient need profile is provided to one or more potential donors through a network of computing systems and/or server systems that is comprised of multiple different computers, wireless devices, cellular telephones, digital telephones, two-way pagers, personal digital assistants, server computers, or any desired combination of these devices, that are interconnected using a network, such as network 130 of FIG. 1. As discussed above, network 130 can be any network or network system that is of interest to a user such as a Local Area Network (LAN), a Wide Area Network (WAN), a public network, such as the Internet, a private network, a combination of network types, or other network capable of allowing communication between two or more computing systems, whether available or known at the time of filing or as later developed.

In other embodiments, at THE VERIFIED PATIENT NEED PROFILE IS PROVIDED TO ONE OR MORE POTENTIAL DONORS THROUGH THE HEALTHCARE MANAGEMENT SYSTEM OPERATION 217 the verified patient need profile is provided to one or more potential donors through e-mail or through text messaging.

In other embodiments, at THE VERIFIED PATIENT NEED PROFILE IS PROVIDED TO ONE OR MORE POTENTIAL DONORS THROUGH THE HEALTHCARE MANAGEMENT SYSTEM OPERATION 217 the verified patient need profile is provided to one or more potential donors through any method, apparatus, process or mechanism for transferring data and/or text from one or more devices, computing systems, server systems, databases, web site/web functions and/or any devices having a data storage capability to one or more other devices, computing systems, server systems, databases, web site/web functions and/or any devices having a data storage capability, whether known at the time of filing or as thereafter developed.

In one embodiment, once the verified patient need profile of THE VERIFIED PATIENT NEED PROFILE DATA IS USED TO CREATE A VERIFIED PATIENT NEED PROFILE OPERATION 213 is made available to potential donors including, but not limited to: the healthcare service provider to whom the funds are owed; potential donors designated by the healthcare consumer, such as family and friends; pre-registered potential donors that have indicated a desire to help specific verified types of patients and/or healthcare consumers with verified healthcare expense needs; pre-registered potential donors who have indicated a desire to help any verified patients and/or healthcare consumers with any verified healthcare expense needs; and/or various other potential donor parties and/or organizations associated with specific types of patients/healthcare needs or general patient/healthcare assistance at THE VERIFIED PATIENT NEED PROFILE IS PROVIDED TO ONE OR MORE POTENTIAL DONORS THROUGH THE HEALTHCARE MANAGEMENT SYSTEM OPERATION 217, process flow proceeds to AT LEAST ONE DONOR DECIDES TO MAKE A DONATION OPERATION 219.

In one embodiment, at AT LEAST ONE DONOR DECIDES TO MAKE A DONATION OPERATION 219, at least one of the potential donors of THE VERIFIED PATIENT NEED PROFILE IS PROVIDED TO ONE OR MORE POTENTIAL DONORS THROUGH THE HEALTHCARE MANAGEMENT SYSTEM OPERATION 217 indicates that they would like to make a donation.

In one embodiment, at AT LEAST ONE DONOR DECIDES TO MAKE A DONATION OPERATION 219, the potential donors are provided the ability to securely make donations to the patient's healthcare expenses directly, in one embodiment, through the patient need profile of THE VERIFIED PATIENT NEED PROFILE IS PROVIDED TO ONE OR MORE POTENTIAL DONORS THROUGH THE HEALTHCARE MANAGEMENT SYSTEM OPERATION 217.

In one embodiment, at AT LEAST ONE DONOR DECIDES TO MAKE A DONATION OPERATION 219, at least one of the potential donors of THE VERIFIED PATIENT NEED PROFILE IS PROVIDED TO ONE OR MORE POTENTIAL DONORS THROUGH THE HEALTHCARE MANAGEMENT SYSTEM OPERATION 217 indicates that they would like to make a donation via a display of the patient need profile displayed on a display device such as display device 165. associated with a potential donor computing system, such as potential donor computing system 150 of FIG. 1, using a user interface devices such as a keyboard, mouse, touchpad, or any other device capable of providing user input to a computing system or for translating user actions into computing system operations, whether known at the time of filing or as developed later.

In one embodiment, once at least one of the potential donors of THE VERIFIED PATIENT NEED PROFILE IS PROVIDED TO ONE OR MORE POTENTIAL DONORS THROUGH THE HEALTHCARE MANAGEMENT SYSTEM OPERATION 217 indicates that they would like to make a donation at AT LEAST ONE DONOR DECIDES TO MAKE A DONATION OPERATION 219, process flow proceeds to THE DONATION IS TRANSFERRED TO THE HEALTHCARE SERVICE PROVIDER TO WHOM THE HEALTHCARE CONSUMER OWES THE HEALTHCARE EXPENSES THROUGH THE PAYMENT MECHANISM OPERATION 221.

In one embodiment, at THE DONATION IS TRANSFERRED TO THE HEALTHCARE SERVICE PROVIDER TO WHOM THE HEALTHCARE CONSUMER OWES THE HEALTHCARE EXPENSES THROUGH THE PAYMENT MECHANISM OPERATION 221 the donation funds of AT LEAST ONE DONOR DECIDES TO MAKE A DONATION OPERATION 219 are collected via credit card, wire transfer, bank transfer, bill pay, check, PayPal™, or any other method, means, and or mechanism for transferring funds as discussed herein, and/or as known in the art at the time of filing, and/or as developed after the time of filing, and the donated funds are then transferred to the healthcare services provider by any of the one or more payment mechanisms established by, and/or through, the healthcare management system and/or healthcare management system provider of A PAYMENT MECHANISM IS ESTABLISHED FOR DONORS TO MAKE PAYMENTS DIRECTLY TO A HEALTHCARE SERVICE PROVIDER TO WHOM THE HEALTHCARE CONSUMER OWES FUNDS OPERATION 215.

In one embodiment, once the donation funds of AT LEAST ONE DONOR DECIDES TO MAKE A DONATION OPERATION 219 are collected and transferred to the healthcare services provider at THE DONATION IS TRANSFERRED TO THE HEALTHCARE SERVICE PROVIDER TO WHOM THE HEALTHCARE CONSUMER OWES THE HEALTHCARE EXPENSES THROUGH THE PAYMENT MECHANISM OPERATION 221, process flow proceeds to THE HEALTHCARE CONSUMER'S ACCOUNT WITH THE HEALTHCARE SERVICE PROVIDER AND A BALANCE OWED AMOUNT IN THE PATIENT NEED PROFILE ARE UPDATED TO REFLECT THE DONATION OPERATION 223.

In one embodiment, at THE HEALTHCARE CONSUMER'S ACCOUNT WITH THE HEALTHCARE SERVICE PROVIDER AND A BALANCE OWED AMOUNT IN THE PATIENT NEED PROFILE ARE UPDATED TO REFLECT THE DONATION OPERATION 223 any funds contributed by a donor at THE DONATION IS TRANSFERRED TO THE HEALTHCARE SERVICE PROVIDER TO WHOM THE HEALTHCARE CONSUMER OWES THE HEALTHCARE EXPENSES THROUGH THE PAYMENT MECHANISM OPERATION 221 are credited to the healthcare consumer's account with the healthcare service provider, the account balance is updated, and the patient is informed of the deposited funds and any remaining balance.

In one embodiment, once any funds contributed by a donor at THE DONATION IS TRANSFERRED TO THE HEALTHCARE SERVICE PROVIDER TO WHOM THE HEALTHCARE CONSUMER OWES THE HEALTHCARE EXPENSES THROUGH THE PAYMENT MECHANISM OPERATION 221 are credited to the healthcare consumer's account with the healthcare service provider, the account balance is updated, and the patient is informed of the deposited funds and any remaining balance at THE HEALTHCARE CONSUMER'S ACCOUNT WITH THE HEALTHCARE SERVICE PROVIDER AND A BALANCE OWED AMOUNT IN THE PATIENT NEED PROFILE ARE UPDATED TO REFLECT THE DONATION OPERATION 223, process flow proceeds to THE DONOR IS NOTIFIED OF THE SUCCESSFUL DONATION, AND/OR THE UPDATED BALANCE OWED, AND/OR IS PROVIDED SUPPORTING DOCUMENTATION OPERATION 225.

In one embodiment, at THE DONOR IS NOTIFIED OF THE SUCCESSFUL DONATION, AND/OR THE UPDATED BALANCE OWED, AND/OR IS PROVIDED SUPPORTING DOCUMENTATION OPERATION 225 an updated balance of funds owed is included in an updated patient need profile and any donors making a donation are provided documentation data indicating the donation, the remaining balance, and any data required for tax purposes.

In one embodiment, once an updated balance of funds owed is included in an updated patient need profile and any donors making a donation are provided documentation data indicating the donation, the remaining balance, and any data required for tax purposes at THE DONOR IS NOTIFIED OF THE SUCCESSFUL DONATION, AND/OR THE UPDATED BALANCE OWED, AND/OR IS PROVIDED SUPPORTING DOCUMENTATION OPERATION 225, process flow proceeds to EXIT OPERATION 230.

In one embodiment, at EXIT OPERATION 230 process for providing a healthcare expense donation network 200 is exited to await new data.

Using process for providing a healthcare expense donation network 200, potential donors are made aware of specific patients in need, whose situations and healthcare expenses are verified through a third party, and the donors are provided an efficient and user friendly way to facilitate providing funds to help the patients with their healthcare expenses and ensuring that the funds are actually used to help pay the patients healthcare expenses by transferring the funds directly to the healthcare service providers to whom the funds are owed. Consequently, using process for providing a healthcare expense donation network 200, potential donors are more likely to become actual donors and more needy patients will be provided the funds they need to avoid financial ruin.

As discussed in more detail above, using the above embodiments, with little or no modification and/or user input, there is considerable flexibility, adaptability, and opportunity for customization to meet the specific needs of various users under numerous circumstances.

In the discussion above, certain aspects of one embodiment include process steps and/or operations and/or instructions described herein for illustrative purposes in a particular order and/or grouping. However, the particular order and/or grouping shown and discussed herein are illustrative only and not limiting. Those of skill in the art will recognize that other orders and/or grouping of the process steps and/or operations and/or instructions are possible and, in some embodiments, one or more of the process steps and/or operations and/or instructions discussed above can be combined and/or deleted. In addition, portions of one or more of the process steps and/or operations and/or instructions can be re-grouped as portions of one or more other of the process steps and/or operations and/or instructions discussed herein. Consequently, the particular order and/or grouping of the process steps and/or operations and/or instructions discussed herein do not limit the scope of the invention as claimed below.

As discussed in more detail above, using the above embodiments, with little or no modification and/or user input, there is considerable flexibility, adaptability, and opportunity for customization to meet the specific needs of various users under numerous circumstances.

The present invention has been described in particular detail with respect to specific possible embodiments. Those of skill in the art will appreciate that the invention may be practiced in other embodiments. For example, the nomenclature used for components, capitalization of component designations and terms, the attributes, data structures, or any other programming or structural aspect is not significant, mandatory, or limiting, and the mechanisms that implement the invention or its features can have various different names, formats, or protocols. Further, the system or functionality of the invention may be implemented via various combinations of software and hardware, as described, or entirely in hardware elements. Also, particular divisions of functionality between the various components described herein are merely exemplary, and not mandatory or significant. Consequently, functions performed by a single component may, in other embodiments, be performed by multiple components, and functions performed by multiple components may, in other embodiments, be performed by a single component.

Some portions of the above description present the features of the present invention in terms of algorithms and symbolic representations of operations, or algorithm-like representations, of operations on information/data. These algorithmic or algorithm-like descriptions and representations are the means used by those of skill in the art to most effectively and efficiently convey the substance of their work to others of skill in the art. These operations, while described functionally or logically, are understood to be implemented by computer programs or computing systems. Furthermore, it has also proven convenient at times to refer to these arrangements of operations as steps or modules or by functional names, without loss of generality.

Unless specifically stated otherwise, as would be apparent from the above discussion, it is appreciated that throughout the above description, discussions utilizing terms such as "obtaining", "verifying", "monitoring", "browsing", "updating", "associating", "analyzing", "defining", "storing", "saving", "displaying", "implementing", "performing", "creating", "assigning", "estimating", "entering", "modifying", "categorizing", "providing", "processing", "accessing", "selecting", "creating", "using", "submitting", "generating", etc., refer to the action and process of a computing system or similar electronic device that manipulates and operates on data represented as physical (electronic) quantities within the computing system memories, resisters, caches or other information storage, transmission or display devices.

Certain aspects of the present invention include process steps or operations and instructions described herein in an algorithmic or algorithmic-like form. It should be noted that the process steps or operations and instructions of the present invention can be embodied in software, firmware, or hardware, and when embodied in software, can be downloaded to reside on and be operated from different platforms used by real time network operating systems.

The present invention also relates to an apparatus or system for performing the operations described herein. This apparatus or system may be specifically constructed for the required purposes, or the apparatus or system can comprise a general purpose system selectively activated or configured/reconfigured by a computer program stored on a computer program product as discussed herein that can be accessed by a computing system or other device.

Those of skill in the art will readily recognize that the algorithms and operations presented herein are not inherently related to any particular computing system, computer architecture, computer or industry standard, or any other specific apparatus. Various general purpose systems may also be used with programs in accordance with the teaching herein, or it may prove more convenient/efficient to construct more specialized apparatuses to perform the required operations described herein. The required structure for a variety of these systems will be apparent to those of skill in the art, along with equivalent variations. In addition, the present invention is not described with reference to any particular programming language and it is appreciated that a variety of programming languages may be used to implement the teachings of the present invention as described herein, and any references to a specific language or languages are provided for illustrative purposes only and for enablement of the contemplated best mode of the invention at the time of filing.

The present invention is well suited to a wide variety of computer network systems operating over numerous topologies. Within this field, the configuration and management of large networks comprise storage devices and computers that are communicatively coupled to similar or dissimilar computers and storage devices over a private network, a LAN, a WAN, a private network, or a public network, such as the Internet.

It should also be noted that the language used in the specification has been principally selected for readability, clarity and instructional purposes, and may not have been selected to delineate or circumscribe the inventive subject matter. Accordingly, the disclosure of the present invention is intended to be illustrative, but not limiting, of the scope of the invention, which is set forth in the claims below.

In addition, the operations shown in the FIG.s, or as discussed herein, are identified using a particular nomenclature for ease of description and understanding, but other nomenclature is often used in the art to identify equivalent operations.

Therefore, numerous variations, whether explicitly provided for by the specification or implied by the specification or not, may be implemented by one of skill in the art in view of this disclosure.

What is claimed is:

1. A computing system implemented process for providing a healthcare expense donation network comprising:
   providing a healthcare management system;
   providing a healthcare consumer access to data indicating healthcare services expenses associated with the healthcare consumer and a healthcare service provider;
   the healthcare consumer determining that they desire donations to help with the healthcare services expenses associated with the healthcare consumer and the healthcare service provider;
   using one or more processors associated with one or more computing systems to provide the healthcare consumer with the capability to provide patient need profile data through the healthcare management system;

obtaining patient need profile data from the healthcare consumer through the healthcare management system;

verifying at least part of the patient need profile data from the healthcare consumer through the healthcare management system;

using one or more processors associated with one or more computing systems to transform at least part of the patient need profile data into a verified patient need profile associated with the healthcare consumer;

using one or more processors associated with one or more computing systems to establish a donor payment mechanism whereby a donor can make a donation to the healthcare service provider on behalf of the healthcare service consumer;

using one or more processors associated with one or more computing systems to distribute data representing the verified patient need profile associated with the healthcare consumer to one or more potential donors; and at least one of the one or more donors making a donation to the healthcare consumer in the form of a payment to the healthcare service provider made through the patient need profile associated with the healthcare consumer and the donor payment mechanism.

2. The computing system implemented process for providing a healthcare expense donation network of claim 1, wherein;

the healthcare management system helps a user healthcare consumer track their healthcare expenses by gathering healthcare expense data from one or more sources.

3. The computing system implemented process for providing a healthcare expense donation network of claim 1, wherein;

patient need profile data provided by the healthcare consumer includes one of more patient need profile data items selected form the group of patient need profile data items consisting of:

the patient's name;
the patient's age;
the patient's DOB (date of birth);
other patient demographic data;
the patient's illness/injury associated with the healthcare service expenses owed;
the provider of the healthcare services for which funds are owed;
images of the patient;
images of the patient's family;
images of the healthcare consumer;
how much the healthcare consumer has already paid;
a balance of how much is owed;
any healthcare benefit plans associated with the patient/ healthcare consumer;
biographical and/or historical information associated with the healthcare consumer, the patient, or the patient's family;
financial data associated with the healthcare consumer;
contact data, associated with any potential donors known by the healthcare consumer; and
data granting the process for providing a healthcare expense donation network, a provider of the process for providing a healthcare expense donation network, or any other party associated with the process for providing a healthcare expense donation network, permission to obtain and/or verify any of the patient need profile data provided by the healthcare consumer from any party or source.

4. The computing system implemented process for providing a healthcare expense donation network of claim 1, wherein;

using one or more processors associated with one or more computing systems to establish a donor payment mechanism includes creating a merchant account for the healthcare services provider through the healthcare management system.

5. The computing system implemented process for providing a healthcare expense donation network of claim 1, wherein;

using one or more processors associated with one or more computing systems to establish a donor payment mechanism includes creating a healthcare consumer account linked to a merchant account for the healthcare services provider through the healthcare management system.

6. The computing system implemented process for providing a healthcare expense donation network of claim 1, wherein;

using one or more processors associated with one or more computing systems to establish a donor payment mechanism includes the healthcare management system acting as a clearing house to distribute donations to the healthcare consumer to the respective healthcare service provider.

7. The computing system implemented process for providing a healthcare expense donation network of claim 1, wherein;

the healthcare management system verifies at least part of the patient need profile data from the healthcare consumer by receiving the data directly from the healthcare service provider.

8. The computing system implemented process for providing a healthcare expense donation network of claim 1, wherein;

the healthcare management system verifies at least part of the patient need profile data from the healthcare consumer by receiving the data directly from EOB (Explanation of Benefits) data.

9. The computing system implemented process for providing a healthcare expense donation network of claim 1, wherein;

the healthcare management system verifies at least part of the patient need profile data from the healthcare consumer by receiving data from a data management system other than the healthcare management system.

10. The computing system implemented process for providing a healthcare expense donation network of claim 9, wherein;

the data management system other than the healthcare management system is a personal financial management system.

11. The computing system implemented process for providing a healthcare expense donation network of claim 9, wherein;

the data management system other than the healthcare management system is a tax preparation system.

12. The computing system implemented process for providing a healthcare expense donation network of claim 1, wherein;

verified patient need profile includes one of more verified patient need profile data items selected form the group of verified patient need profile data items consisting of:

the patient's name;
the patient's age;
the patient's DOB (date of birth);
other patient demographic data;

the patient's illness/injury associated with the healthcare service expenses owed;
the provider of the healthcare services for which funds are owed;
images of the patient;
images of the patient's family;
images of the healthcare consumer;
how much the healthcare consumer has already paid;
a balance of how much is owed;
biographical and/or historical information associated with the healthcare consumer, the patient, or the patient's family; and
financial data associated with the healthcare consumer.

13. A system for providing a healthcare expense donation network comprising:
a healthcare consumer computing system;
a donor computing system;
a healthcare management system;
a process provider computing system, the process provider computing system including at least one processor for executing at least part of a process for providing a healthcare expense donation network, the process for providing a healthcare expense donation network comprising:
providing a healthcare consumer access to data indicating healthcare services expenses associated with the healthcare consumer and a healthcare service provider through the healthcare consumer computing system;
the healthcare consumer determining that they desire donations to help with the healthcare services expenses associated with the healthcare consumer and the healthcare service provider;
providing the healthcare consumer with the capability to provide patient need profile data through the healthcare management system and the healthcare consumer computing system;
obtaining patient need profile data from the healthcare consumer through the healthcare management system and healthcare consumer computing system;
verifying at least part of the patient need profile data from the healthcare consumer through the healthcare management system;
transforming at least part of the patient need profile data into a verified patient need profile associated with the healthcare consumer;
establishing a donor payment mechanism whereby a donor can make a donation to the healthcare service provider on behalf of the healthcare service consumer;
distributing data representing the verified patient need profile associated with the healthcare consumer to a potential donor through the donor computing system; and
the making a donation on behalf of the healthcare consumer through the donor computing system in the form of a payment to the healthcare service provider made through the patient need profile associated with the healthcare consumer and the donor payment mechanism.

14. The system for providing a healthcare expense donation network of claim 13, wherein;
the healthcare management system helps a user healthcare consumer track their healthcare expenses by gathering healthcare expense data from one or more sources.

15. The system for providing a healthcare expense donation network of claim 13, wherein;
patient need profile data provided by the healthcare consumer includes one of more patient need profile data items selected form the group of patient need profile data items consisting of:
the patient's name;
the patient's age;
the patient's DOB (date of birth);
other patient demographic data;
the patient's illness/injury associated with the healthcare service expenses owed;
the provider of the healthcare services for which funds are owed;
images of the patient;
images of the patient's family;
images of the healthcare consumer;
how much the healthcare consumer has already paid;
a balance of how much is owed;
any healthcare benefit plans associated with the patient/healthcare consumer;
biographical and/or historical information associated with the healthcare consumer, the patient, or the patient's family;
financial data associated with the healthcare consumer;
contact data, associated with any potential donors known by the healthcare consumer; and
data granting the process for providing a healthcare expense donation network, a provider of the process for providing a healthcare expense donation network, or any other party associated with the process for providing a healthcare expense donation network, permission to obtain and/or verify any of the patient need profile data provided by the healthcare consumer from any party or source.

16. The system for providing a healthcare expense donation network of claim 13, wherein;
establishing a donor payment mechanism includes creating a merchant account for the healthcare services provider through the healthcare management system.

17. The system for providing a healthcare expense donation network of claim 13, wherein;
establishing a donor payment mechanism includes creating a healthcare consumer account linked to a merchant account for the healthcare services provider through the healthcare management system.

18. The system for providing a healthcare expense donation network of claim 13, wherein;
establishing a donor payment mechanism includes the healthcare management system acting as a clearing house to distribute donations to the healthcare consumer to the respective healthcare service provider.

19. The system for providing a healthcare expense donation network of claim 13, wherein;
the healthcare management system verifies at least part of the patient need profile data from the healthcare consumer by receiving the data directly from the healthcare service provider.

20. The system for providing a healthcare expense donation network of claim 13, wherein;
the healthcare management system verifies at least part of the patient need profile data from the healthcare consumer by receiving the data directly from EOB (Explanation of Benefits) data.

21. The system for providing a healthcare expense donation network of claim 13, wherein;
the healthcare management system verifies at least part of the patient need profile data from the healthcare consumer by receiving data from a data management system other than the healthcare management system.

22. The system for providing a healthcare expense donation network of claim 21, wherein;

the data management system other than the healthcare management system is a personal financial management system.

23. The system for providing a healthcare expense donation network of claim 21, wherein;
the data management system other than the healthcare management system is a tax preparation system.

24. The system for providing a healthcare expense donation network of claim 13, wherein;
verified patient need profile includes one of more verified patient need profile data items selected form the group of verified patient need profile data items consisting of:
the patient's name;
the patient's age;
the patient's DOB (date of birth);
other patient demographic data;
the patient's illness/injury associated with the healthcare service expenses owed;
the provider of the healthcare services for which funds are owed;
images of the patient;
images of the patient's family;
images of the healthcare consumer;
how much the healthcare consumer has already paid;
a balance of how much is owed;
biographical and/or historical information associated with the healthcare consumer, the patient, or the patient's family; and
financial data associated with the healthcare consumer.

25. A healthcare expense donation network comprising:
a healthcare consumer computing system;
a donor computing system;
a process provider computing system 120; the process provider computing system including at least one processor for executing at least part of a process for providing a healthcare expense donation network, the process for providing a healthcare expense donation network comprising:
providing a healthcare consumer access to data indicating healthcare services expenses associated with the healthcare consumer and a healthcare service provider through the healthcare consumer computing system;
the healthcare consumer determining that they desire donations to help with the healthcare services expenses associated with the healthcare consumer and the healthcare service provider;
providing the healthcare consumer with the capability to provide patient need profile data through the healthcare management system and the healthcare consumer computing system;
obtaining patient need profile data from the healthcare consumer through the healthcare management system and healthcare consumer computing system;
verifying at least part of the patient need profile data from the healthcare consumer through the healthcare management system;
transforming at least part of the patient need profile data into a verified patient need profile associated with the healthcare consumer;
establishing a donor payment mechanism whereby a donor can make a donation to the healthcare service provider on behalf of the healthcare service consumer;
distributing data representing the verified patient need profile associated with the healthcare consumer to a potential donor through the donor computing system; and
the making a donation on behalf of the healthcare consumer through the donor computing system in the form of a payment to the healthcare service provider made through the patient need profile associated with the healthcare consumer and the donor payment mechanism.

26. The healthcare expense donation network of claim 25, wherein;
the healthcare management system helps a user healthcare consumer track their healthcare expenses by gathering healthcare expense data from one or more sources.

27. The healthcare expense donation network of claim 25, wherein;
patient need profile data provided by the healthcare consumer includes one of more patient need profile data items selected form the group of patient need profile data items consisting of:
the patient's name;
the patient's age;
the patient's DOB (date of birth);
other patient demographic data;
the patient's illness/injury associated with the healthcare service expenses owed;
the provider of the healthcare services for which funds are owed;
images of the patient;
images of the patient's family;
images of the healthcare consumer;
how much the healthcare consumer has already paid;
a balance of how much is owed;
any healthcare benefit plans associated with the patient/healthcare consumer;
biographical and/or historical information associated with the healthcare consumer, the patient, or the patient's family;
financial data associated with the healthcare consumer;
contact data, associated with any potential donors known by the healthcare consumer; and
data granting the process for providing a healthcare expense donation network, a provider of the process for providing a healthcare expense donation network, or any other party associated with the process for providing a healthcare expense donation network, permission to obtain and/or verify any of the patient need profile data provided by the healthcare consumer from any party or source.

28. The healthcare expense donation network of claim 25, wherein;
establishing a donor payment mechanism includes creating a merchant account for the healthcare services provider through the healthcare management system.

29. The healthcare expense donation network of claim 25, wherein;
establishing a donor payment mechanism includes creating a healthcare consumer account linked to a merchant account for the healthcare services provider through the healthcare management system.

30. The healthcare expense donation network of claim 25, wherein;
establishing a donor payment mechanism includes the healthcare management system acting as a clearing house to distribute donations to the healthcare consumer to the respective healthcare service provider.

31. The healthcare expense donation network of claim 25, wherein;
  the healthcare management system verifies at least part of the patient need profile data from the healthcare consumer by receiving the data directly from the healthcare service provider.

32. The healthcare expense donation network of claim 25, wherein;
  the healthcare management system verifies at least part of the patient need profile data from the healthcare consumer by receiving the data directly from EOB (Explanation of Benefits) data.

33. The healthcare expense donation network of claim 25, wherein;
  the healthcare management system verifies at least part of the patient need profile data from the healthcare consumer by receiving data from a data management system other than the healthcare management system.

34. The healthcare expense donation network of claim 33, wherein;
  the data management system other than the healthcare management system is a personal financial management system.

35. The healthcare expense donation network of claim 33, wherein;
  the data management system other than the healthcare management system is a tax preparation system.

36. The healthcare expense donation network of claim 25, wherein;
  verified patient need profile includes one of more verified patient need profile data items selected form the group of verified patient need profile data items consisting of:
  the patient's name;
  the patient's age;
  the patient's DOB (date of birth);
  other patient demographic data;
  the patient's illness/injury associated with the healthcare service expenses owed;
  the provider of the healthcare services for which funds are owed;
  images of the patient;
  images of the patient's family;
  images of the healthcare consumer;
  how much the healthcare consumer has already paid;
  a balance of how much is owed;
  biographical and/or historical information associated with the healthcare consumer, the patient, or the patient's family; and
  financial data associated with the healthcare consumer.

\* \* \* \* \*

UNITED STATES PATENT AND TRADEMARK OFFICE
CERTIFICATE OF CORRECTION

PATENT NO.        : 8,209,194 B1
APPLICATION NO.   : 12/845309
DATED             : June 26, 2012
INVENTOR(S)       : Dawn M. Nidy et al.

It is certified that error appears in the above-identified patent and that said Letters Patent is hereby corrected as shown below:

In the Claims
Column 31, Line 34, Claim 3, replace "one of more" with --one or more--;
Column 31, Line 35, Claim 3, replace "form" with --from--;
Column 32, Line 61, Claim 12, replace "one of more" with --one or more--;
Column 32, Line 62, Claim 12, replace "form" with --from--;
Column 33, Line 65, Claim 15, replace "one of more" with --one or more--;
Column 33, Line 66, Claim 15, replace "form" with --from--;
Column 35, Line 10, Claim 24, replace "one of more" with --one or more--;
Column 35, Line 11, Claim 24, replace "form" with --from--;
Column 36, Line 19, Claim 27, replace "one of more" with --one or more--;
Column 36, Line 20, Claim 27, replace "form" with --from--;
Column 38, Line 5, Claim 36, replace "one of more" with --one or more--; and
Column 38, Line 6, Claim 36, replace "form" with --from--.

Signed and Sealed this
Third Day of June, 2014

Michelle K. Lee
*Deputy Director of the United States Patent and Trademark Office*